US011911050B2

(12) United States Patent
Amanatullah et al.

(10) Patent No.: US 11,911,050 B2
(45) Date of Patent: Feb. 27, 2024

(54) SYSTEM FOR TOTAL KNEE REPLACEMENT

(71) Applicant: Arthrology Consulting, LLC, Palo Alto, CA (US)

(72) Inventors: Derek Amanatullah, Palo Alto, CA (US); Thomas J Blumenfeld, Palo Alto, CA (US)

(73) Assignee: Knimble Designs, Inc., Dover, DE (US)

( * ) Notice: Subject to any disclaimer, the term of this patent is extended or adjusted under 35 U.S.C. 154(b) by 133 days.

(21) Appl. No.: 17/515,205

(22) Filed: Oct. 29, 2021

(65) Prior Publication Data
US 2022/0133338 A1 May 5, 2022

Related U.S. Application Data

(60) Provisional application No. 63/108,243, filed on Oct. 30, 2020.

(51) Int. Cl.
*A61B 17/17* (2006.01)
(52) U.S. Cl.
CPC ...... *A61B 17/1764* (2013.01); *A61B 17/1721* (2013.01); *A61B 17/1742* (2013.01)

(58) Field of Classification Search
CPC ............ A61B 17/1764; A61B 17/1721; A61B 17/1742
See application file for complete search history.

(56) References Cited

U.S. PATENT DOCUMENTS

2015/0057756 A1* 2/2015 Lang ........................ A61F 2/389
623/18.11

* cited by examiner

*Primary Examiner* — Sameh R Boles
(74) *Attorney, Agent, or Firm* — Run8 Patent Group, LLC; Peter Miller

(57) ABSTRACT

Once variation of a system for total knee replacement includes: a first alignment guide defining first set of guides that locate a first set of pins on a first bone of a joint in extension and defining a reference surface relative to the first set pin guides; a second alignment guide constrained relative to the first alignment guide by the reference surface and defining a second set of guides, relative to the first set of guides, that locate a second set of pins on a second bone of the joint; a first cut guide located by the first set of pins and defining a first cut plane for resecting the first bone; and a second cut guide located by the second set of pins and defining a second cut plane, linearly offset from the first cut plane, for resecting the second bone.

20 Claims, 8 Drawing Sheets

SYSTEM FOR TOTAL KNEE REPLACEMENT

CROSS-REFERENCE TO RELATED APPLICATIONS

This application claims priority to U.S. Provisional Patent Application No. 63/108,243, filed on 30 Oct. 2020, which is incorporated in its entirety by this reference.

TECHNICAL FIELD

This invention relates generally to the field of arthroplasty and more specifically to a new and useful predictive total knee alignment and balancing system in the field of arthroplasty.

DESCRIPTION OF THE EMBODIMENTS

Figure 1:
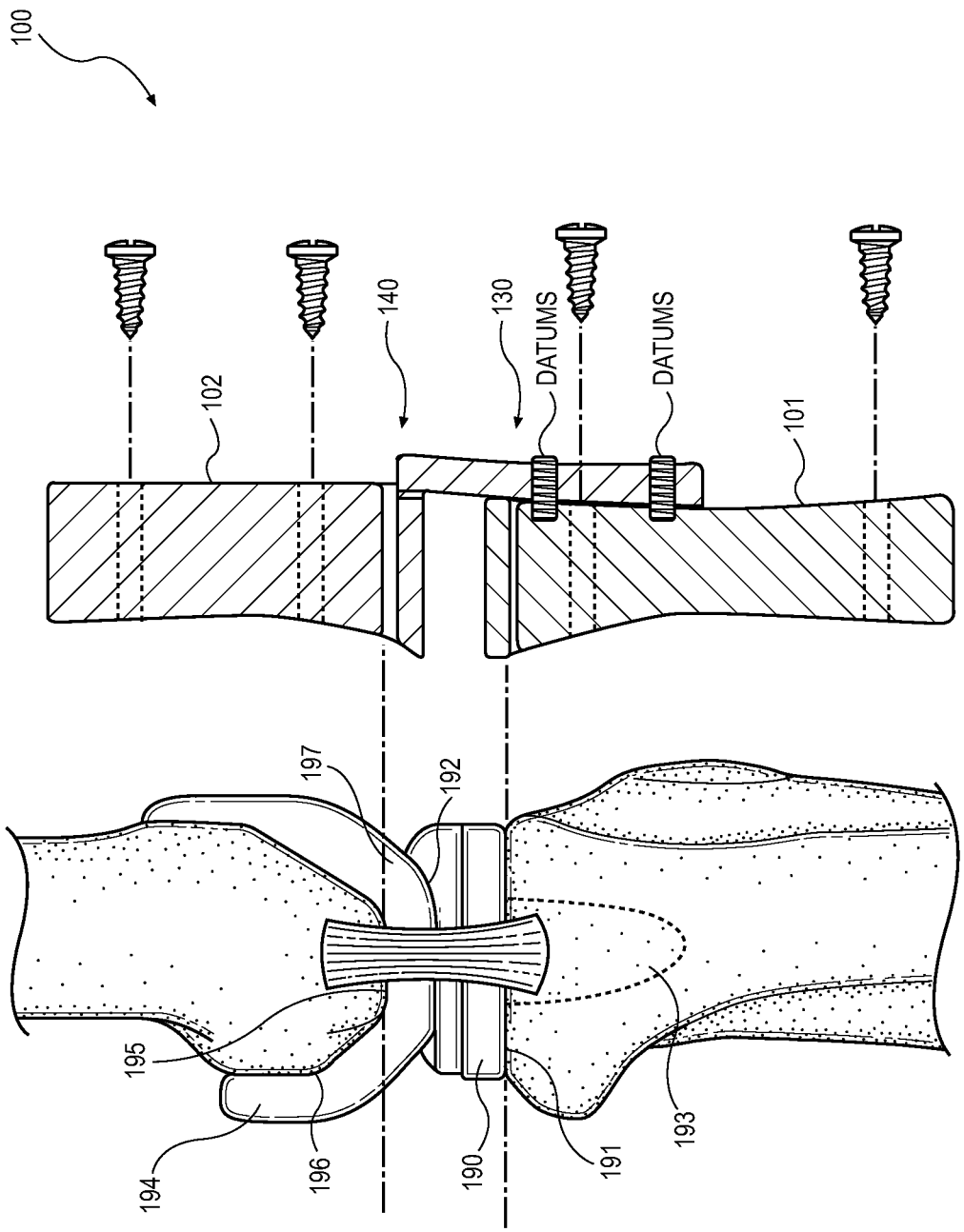
FIG. 1 is a schematic representation of a system.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System

As shown in FIGS. 1-4, a system 100 for total knee replacement includes: an artificial tibial component 190 defining an inner proximal tibial face 191; an artificial femoral component defining an inner distal femoral face 195, an inner posterior femoral face 196, and an inner anterior face and configured to mate with the artificial tibial component 190; and a first guide unit 101 configured for temporary installation on a tibia and defining a proximal tibial cut guide 130 that locates a blade during resection of the tibia to form a proximal tibial face.

The system 100 also includes a second guide unit 102: configured to reference against the first guide unit 101; configured for temporary installation on a femur; and defining a distal femoral cut guide 140 offset from the proximal tibial cut guide 130 by a distance between the inner proximal tibial face 191 of the artificial tibial component 190 and the inner distal femoral face 195 of the artificial femoral component in an extension position and that locates a blade during resection of the femur to form a distal femoral face.

The system 100 further includes a third guide unit 103: defining a tibial-side face configured to mate against the proximal tibial face; defining a femoral-side face configured to mate against the distal femoral face and angularly offset from the tibial-side face by an intermediate angle between flexion and extension; defining a wedge-geometry between the tibial-side face and the femoral-side face corresponding to a geometry between the inner proximal tibial face 191 of the artificial tibial component 190 and the inner distal femoral face 195 of the artificial femoral component in the intermediate position; and defining a posterior femoral cut guide 160 positioned relative to the femoral-side face according to a position of the inner posterior femoral face 196 relative to the inner distal femoral face 195 of the artificial femoral component and that locates a blade during resection of the femur to form a posterior femoral face.

2. Applications

Generally, the system 100 for total knee replacement includes: a set of artificial tibial and femoral components; a sequence of guides that each locate (e.g., guide, constrain) paths of blades or other tools for resection of bone—relative to faces resulting from preceding bone resections during a knee replacement surgery—based on the geometries of the artificial tibial and femoral components. The system 100 can further include (or interface with) a tension tool 105 configured to insert between a patient's tibia and femur and to measure and/or set tension on the adjacent medial ligament (i.e., the medial collateral ligament, or MCL) and lateral ligament (i.e., the lateral collateral ligament, or LCL) in the patient's knee during a total knee replacement surgery.

By implementing the tension tool 105 to set the medial ligament and lateral ligament to target tensions in extension before placing the second guide unit 102 relative to the first guide unit 101 and fastening the second guide unit 102 to the femur, the surgeon may: achieve spacing between the tibia and femur that yield balanced and target tensions across the medial ligament and lateral ligament in extension; locate the distal femoral cut guide 140—and therefore the resulting distal femoral face—at a position offset (e.g., and parallel) from the proximal tibial face—previously cut with the proximal tibial cut guide 130 of the first guide unit 101—that matches the offset between the inner distal femoral face 195 and the inner proximal tibial face 191 of the artificial femoral and tibial components, respectively; and thus ensure with high accuracy that the tensions across the medial ligament and lateral ligament when the artificial knee is installed in a patient and located in extension are balanced and approximate their corresponding target tensions in extension.

Similarly, by implementing the tension tool 105 to set the medial ligament and lateral ligament to target tensions (or strains, stresses) in an intermediate position (between extension and flexion) before placing the third guide unit 103 relative to the distal femoral face and fastening the third guide unit 103 to the femur, the surgeon may: achieve spacing between the tibia and femur that yield balanced and target tensions across the medial ligament and lateral ligament in this intermediate position; locate the posterior femoral cut guide 160—and therefore the resulting posterior femoral face—at a position offset from the distal femoral and proximal tibial faces—previously cut according to the first and second guide units 101, 102—that matches the offsets between the inner posterior and inner distal femoral faces 196, 195 of the artificial femoral components and the inner proximal tibial face 191 of the artificial tibial component 190; and thus ensure with high accuracy that the tensions across the medial ligament and lateral ligament when the artificial knee is installed in a patient and located in this intermediate position are balanced and approximate their corresponding target tensions in this position.

Therefore, the system 100 can include a set of guides: matched to absolute and relative geometries of artificial tibial and femoral components over a range of motion; and configured to mate to other guides in the set and/or to bony faces cut according to guides previously implemented during a knee replacement in order to match bony cuts completed during the surgery to the absolute and relative geometries of the artificial tibial and femoral components over a range of motion. Furthermore, the system 100 can include or interface with a tension tool 105 that sets tensions on the medial ligament and lateral ligament when a guide is placed on a patient such that these tensions on the medial ligament and lateral ligament are accurately reproduced when the artificial tibial and femoral components are finally implanted in the patient and occupying similar positions.

Therefore, the guides, artificial components, and tension tool 105 can: quantify relationships between force and ligament strain in a knee over a range of motion; account for ligament tension when a surgeon performs bony cuts; enable co-planar distal femoral, proximal tibia, and posterior femoral cuts based on ligament tension; and thus accurately and repeatably yield collateral ligaments tensed according to the surgeon's specified targets (e.g., equally-tensed) over the range of motion of the patient's knee following a total knee replacement.

The system 100 is described herein with regard to total knee replacement surgeries. However, the system 100 of guides, artificial components, and tension tool 105 can be configured for resection of bony tissue and implantation of artificial joints during surgeries of other types.

Furthermore, the system 100 is first described: with first and second guide units 101, 102 that are both first pinned to a tibia and femur in relative positions and include cut guides that define proximal tibial and distal femoral cut planes 132, 142; and a third guide that both references the resected proximal tibial and distal femoral faces and includes a cut guide that defines a posterior femoral cut plane 162. Accordingly, the system 100 can include a set of linked guide units that collectively define a sequence of tibial and femoral cut guides that approximate known relative geometries of component-to-bone and component-to-component surfaces of artificial tibial and femoral components such that tensions on the medial and lateral ligaments of the knee when the set of linked cut guides are pinned to the tibia and femur early in a surgery approximate b) the same tensions on the medial and lateral ligaments when the artificial tibial and femoral components are installed in the knee upon conclusion of the surgery.

However and as described below, the system 100 can instead include: proximal tibial and distal femoral alignment guides 110, 120 that define pin guides for locating pins (e.g., straight, tapered, or eccentric pins) in relative positions on the tibia and femur; proximal tibial and distal femoral cut guides 130, 140 that are located on the tibia and femur via these pins and define proximal tibial and distal femoral cut planes 132, 142; a posterior femoral alignment guide that references the resected proximal tibial and distal femoral faces and defines pin guides for locating pins in a relative position on the femur; and a posterior femoral cut guide 160 that is located on the femur via these pins and defines a posterior femoral cut plane 162. Accordingly, the system 100 can include a set of linked alignment and cut guide units that collectively define a sequence of linked pin locations that locate tibial and femoral cut guides that approximate known relative geometries of component-to-bone and component-to-component surfaces of artificial tibial and femoral components such that a) tensions on the medial and lateral ligaments of the knee when the set of linked alignment guides are pinned to the tibia and femur earlier in the surgery approximate b) the same tensions on the medial and lateral ligaments when the artificial tibial and femoral components are installed in the knee upon conclusion of the surgery.

Furthermore, the system 100 is described as including a set of physical alignment and/or cut guides. However, the system 100 can additionally or alternatively include analogous virtual alignment and/or cut guides, such as for virtual alignment with boney features to define virtual cut planes and/or virtual cut axes during a robotically-controlled surgery.

3. Tension Tool

The tension tool 105 can include: a first internal jaw (or "spoon"); a second internal jaw adjacent the first internal jaw; a scale coupled to the second jaw and configured to indicate magnitude of a force between the first and second internal jaws; and an extension mechanism configured to expand the first and second internal jaws.

Figure 4:
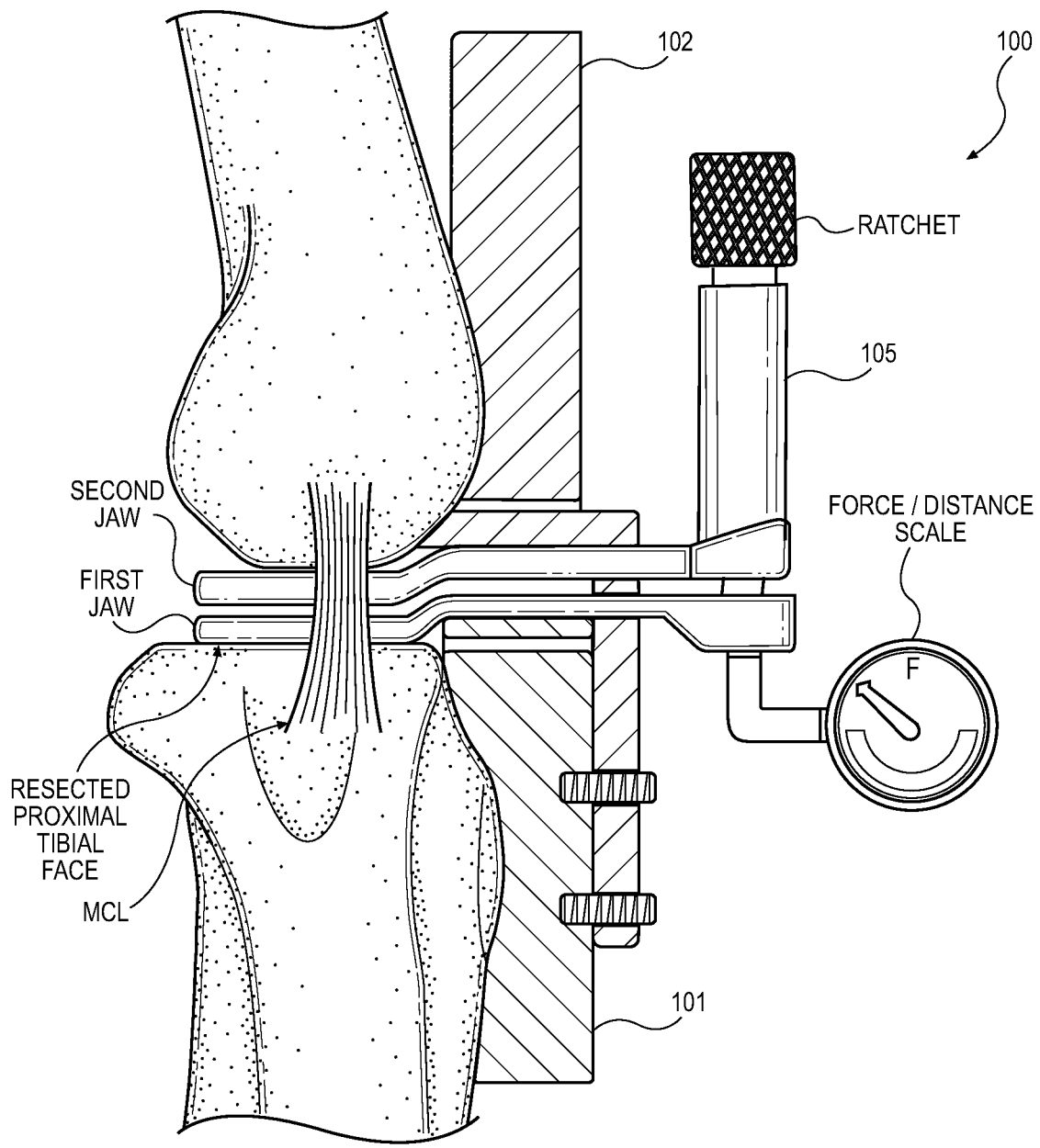
FIG. 4 is a schematic representation of one variation of the system.

In one implementation shown in FIG. 4, the tension tool 105 further includes a rigid housing. The first internal jaw is mounted to the distal end of the housing, and the second internal jaw slides along the housing and includes a nut. In this implementation, the extension mechanism includes: a screw that engages the nut of the second internal jaw to drive the second internal jaw along the housing when the screw is rotated; and a ratchet that rotates the screw by a fixed angular distance per "click."

In this implementation, the scale can includes: a digital micrometer coupled to a lead screw and/or the second internal jaw and configured to track a linear distance traversed by the second internal jaw responsive to operation of the ratchet; a strain gauge (or load cell, etc.) coupled to the first internal jaw and configured to measure a force applied to the first internal jaw; and a controller configured to generate a plot of force applied to the first internal jaw versus linear distance traversed by the second jaw—that is, a stress-strain curve for an adjacent ligament in a knee. In this implementation, the tension tool 105 can also include: a display configured to render the plot; and/or or a wireless communication module configured to stream data from this plot to a remote device (e.g., a display located in the surgical space) that renders the plot in (near) real-time. Thus, in this implementation, a surgeon may: close the first and second jaws; insert the first and second internal jaws between a patient's femur and tibia on the medial side of the patient's knee; rotate the ratchet to expand the internal jaws to engage the tibia and femur and then tension the medial ligament; and lock the ratchet once the tension tool 105 indicates a target absolute force, which corresponds to a target tension on the adjacent medial ligament.

In another example, the surgeon may rotate the ratchet forward, which expands the internal jaws to engage the tibia and femur and then tension the medial ligament; the tension tool 105 derives a stress-strain curve for the medial ligament based on the expansion distance and measures force between the first and second internal jaws as the surgeon expands the tension tool 105. Once the stress-strain curve calculated and rendered by the tension tool 105 (or on the remote device) indicates that the medial ligament is approaching plastic deformation, the surgeon may rotate the ratchet in reverse to return tension on the adjacent ligament to a target position on the stress-strain curve, such as near a neutral or "center" position on this stress-strain curve.

In another implementation, the scale includes: a strain gauge (or load cell, etc.) coupled to the first internal jaw and configured to measure a force applied to the first internal jaw; and a display configured to render this force in real-time and/or a wireless communication module configured to stream force values measured by the strain gauge to a remote device that renders these force values in (near) real-time. In a similar implementation, the scale includes: an analog dial; and a beam extending between the first internal jaw and the analog dial and configured to sweep the analog dial through a range of angular positions corresponding to a magnitude of deflection of the first internal jaw on the housing when the first and second internal jaws are expanded and compressed between a femur and tibia.

Alternatively, the tension tool 105 can include a laminar spreader that indicates change in distance of the set of internal jaws.

However, the tension tool 105 can define any other format and can indicate force magnitude on the first and second jaws and/or change in distance across the first and second jaws—and therefore tension or change in tension on an adjacent ligament—in any other way.

3.1 Double Tensioner

In one variation, the two tension tools 105 are rigidly connected by a bridge that laterally offsets two tension tools 105 by a distance approximating the offset between a patient's lateral and medial femoral condyles.

In one example, a rigid bridge of fixed width is selected from a set of bridges of different widths based on a width of the patient's femoral condyle peaks, such as derived from a preoperative scan or measured intraoperatively by the surgeon. In another example, the bridge is adjustable in width and includes: a first end that rigidly locates a first instance of the tension tool 105; a second end that rigidly locates a second instance of the tension tool 105; and a micrometer or other screw that couples the first and second ends and enables manual adjustment of the width of the bridge and thus the distance between the first and second instances of the tension tool 105.

Therefore, in this variation, the surgeon may: fix the first and second instances of the tension tool 105 at a target offset distance—based on the patient's physiology—via the bridge; insert and retain both instances of the tension tool 105 between the medial and lateral sides of the patient's femur and tibia; and thus set tension on the medial ligament and lateral ligament concurrently via this tension tool 105 assembly.

4. Surgical Guide Set

As described above, the system 100 also includes a set of surgical guides.

4.1 First Guide Unit: Proximal Tibial Cut

Figure 2:
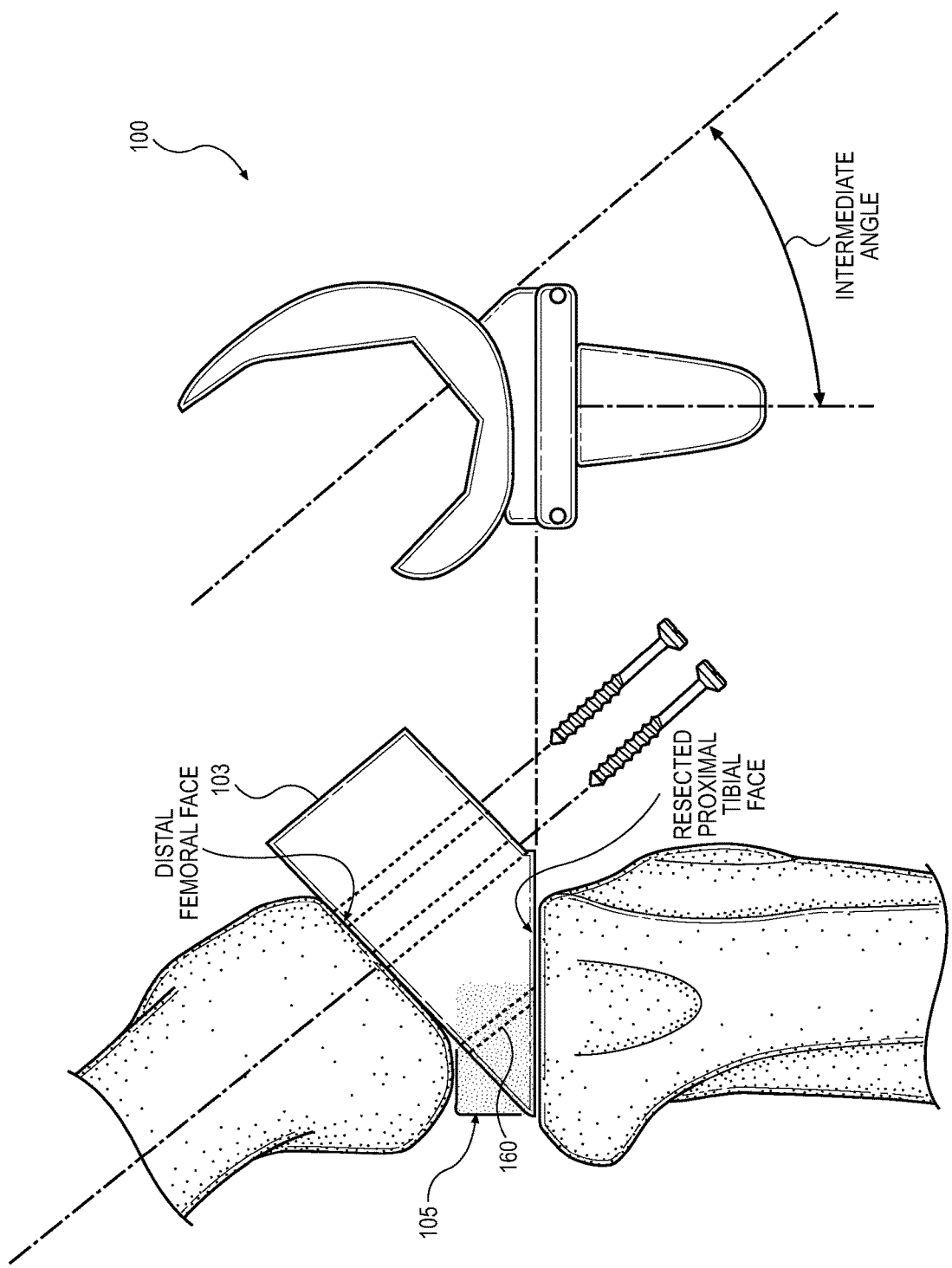
FIG. 2 is a schematic representation of one variation of the system.

As shown in FIGS. 1, 2, and 4, the first guide unit 101 includes: a proximal tibial cut guide 130 that locates a blade (e.g., a reciprocating saw) along a cut plane when resecting the proximal end of a tibia to produce a proximal tibial face configured to mate with a tibial component; a first set of datums offset from the proximal tibial cut guide 130 cut by known lateral and longitudinal distances; and a set of pin receptacles configured to receive pins or other fasteners to temporarily fasten and locate the first guide unit 101 on a tibia.

4.2 Second Guide Unit: Distal Femoral Cut

As shown in FIGS. 1, 2, and 4, the second guide unit 102 includes: a distal femoral cut guide 140 that locates a blade along a cut plane when resecting the distal end of a femur to produce a distal femoral face configured to mate with a inner distal femoral face 195 of a femoral component; a second set of datums offset from the distal femoral cut guide 140 cut by known lateral and longitudinal distances and configured to mate with the first set of datums in the first guide unit 101 and thus locate the distal femoral cut guide 140 relative (e.g., parallel) to and longitudinally offset from the proximal tibial cut guide 130 by a longitudinal distance prescribed by a geometry of artificial tibial and femoral components in extension; and a set of pin receptacles configured to receive pins or other fasteners to temporarily fasten and locate the second guide unit 102 on a femur.

More specifically, when assembled, the first and second guide units 101, 102 can define proximal tibial and distal femoral cut planes 132, 142 that are offset by a geometry that approximates (e.g., is identical to) an offset between inner proximal tibial and inner distal femoral faces 191, 195 of the artificial tibial and femoral components located in extension (e.g., a 0° position). Accordingly, a) tensions across the medial and lateral ligaments of the knee in extension when the first and second guide units 101, 102 are located on the knee may approximate b) tensions across the medial and lateral ligaments of the knee in extension when the artificial femoral component and the artificial tibial component 190 are installed in the knee, all without necessitating further ligament tension measurements, ligament release, or component placement approximations or tests, etc. during the surgery.

In one implementation, the first set of datums and the proximal tibial cut guide 130 are physically coextensive; and the second set of datums includes a tongue extending longitudinally from the second guide unit 102 and configured to seat in the proximal tibial cut guide 130 (once the tibia is resected) in order to locate the distal femoral cut guide 140 relative to the proximal tibial cut guide 130.

In another implementation, the first and second sets of datums include mechanical and/or magnetic reference features that cooperate to kinematically locate the second guide unit 102 relative to the first guide unit 101.

In yet another implementation: the first set of datums are integrated into the first guide unit 101; the second set of datums are integrated into the second guide unit 102; and an intermediate locator mates to the first and second sets of guides to locate the second guide unit 102 relative to the first guide unit 101—and thus locate the distal femoral cut guide 140 relative to the proximal tibial cut guide 130. Thus, in this implementation, the first guide unit 101 can remain fastened to the tibia after the proximal tibial cut is completed, and the intermediate locator can be removed but the second guide unit 102 can remain fastened to the femur after the distal femoral cut is completed.

4.3 Third Guide Unit: Posterior Femoral Cut

Figure 3:
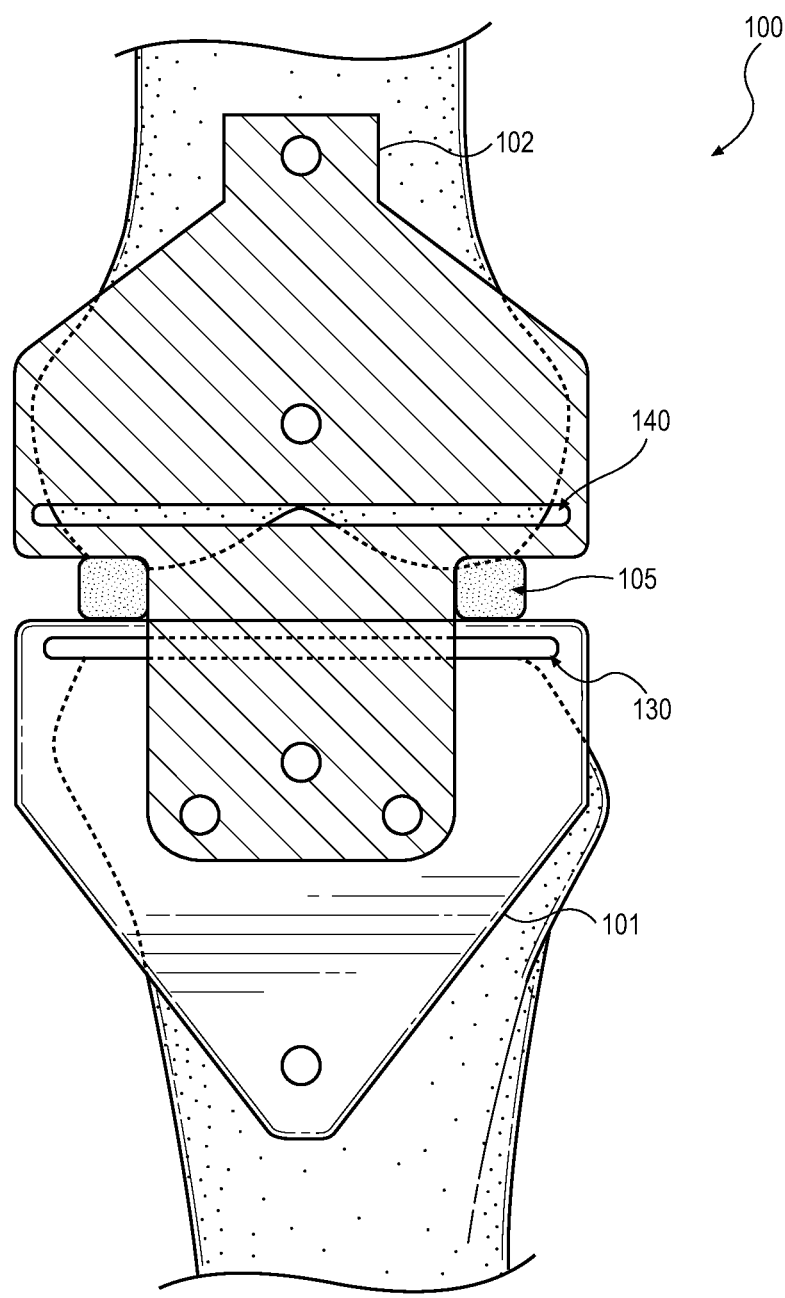
FIG. 3 is a schematic representation of one variation of the system.

As shown in FIG. 3, the system 100 also includes a third guide unit 103.

Generally, the third guide unit 103 defines a tibial side 153 configured to contact the resected proximal tibial face of the tibia, a femoral side 154 configured to contact the resected distal femoral face of the femur, and a posterior femoral cut guide 160 that approximates a geometry of the inner proximal tibial, inner distal femoral, and inner posterior femoral faces of the artificial tibial and femoral components located in an intermediate angle (e.g., a 60° partial-flexion position). Accordingly, a) tensions across the medial and lateral ligaments of the knee in the intermediate angle when the third guide unit 103 is located in the knee may approximate b) tensions across the medial and lateral ligaments of the knee in the intermediate angle when the artificial femoral component and the artificial tibial component 190 are installed in the knee, all without necessitating further ligament tension measurements, ligament release, or component placement approximations or tests, etc. during the surgery.

In one implementation, the third guide unit 103 includes separable first and second elements. In this implementation, the first element defines: a tibial side 153 configured to mate with a proximal tibial face of a tibia following a proximal tibial cut; a femoral side 154 configured to mate with a distal femoral face of a femur following a distal femoral cut; a first set of datums configured to mate with a second set of datums of the second element; and a set of pin receptacles configured to receive pins or other fasteners to temporarily fasten and locate the first element to the distal femoral face. In particular, the tibial and femoral sides 153, 154 of the first element are angularly offset by an intermediate angle (e.g., 60°)—at which a surgeon sets the knee when balancing tension of the medial ligament and the lateral ligament and locating the first element following the distal femoral cut during the surgery. For example, the first element can form a "wedge" configured to insert between the proximal tibial and distal femoral faces and to fasten to the distal femoral face.

In this implementation, the second element: is configured to install over the first element, such as across the tibial side 153 of the first element; defines a second set of datums configured to mate with and locate on the first set of datums of the first element; and defines a posterior femoral cut guide 160 that locates a blade along a cut plane when resecting the posterior end of the femur to produce a posterior femoral face configured to mate with an inner posterior femoral face 196 of the artificial femoral component.

Thus, in this implementation, the second element defining the posterior femoral cut guide 160 can be separable from the first element, thereby reducing a size (or "bulk") of the first element and enabling the surgeon to locate the first element between the femur and tibia with reduced mechanical and visual obstruction. Once the first element is located between the proximal tibial face and the distal femoral face and pinned to the femur with the medial ligament and the lateral ligament balance, the knee can be moved to flexion, thereby moving the proximal tibial face off of the tibial side 153 of the first element and exposing the tibial side 153 of the first element. The surgeon may then locate the second element against the first set of datums on the tibial side 153 of the first element, thereby locating the posterior femoral cut guide 160 at a position relative to the distal femoral face that yields target (e.g., "balanced") tensions on the medial ligament and the lateral ligament at the intermediate position.

Alternatively, the third guide unit 103 can include a singular element defining the tibial side 153, the femoral side 154, and the posterior femoral cut guide 160.

4.4 Fourth Guide Unit: Anterior Femoral Cut

The system 100 can also include a fourth guide unit.

In one implementation, the fourth guide unit defines: an anterior femoral cut guide that locates a blade along a cut plane when resecting the anterior end of the femur to produce an anterior femoral face configured to mate with an anterior inner face of the artificial femoral component; and defines a set of datums (e.g., planar faces) that mate to distal and posterior femoral faces and that locate the anterior femoral cut guide relative to the distal and posterior femoral faces according to the relative positions of the distal, posterior, and anterior inner faces of the artificial femoral component.

4.5 Fifth Guide Unit: Femoral Chamfer Cut Guide

In one variation, the system 100 also includes a fifth guide unit that defines femoral chamfer cut guides that locate a blade along cut planes when resecting chamfers between the anterior and distal femoral faces and between the posterior and distal femoral faces to produce chamfers on the distal end of the femur.

4.6 Sixth Guide Unit: Femoral Channel Guide

In one variation, the system 100 additionally or alternatively includes a sixth guide unit that: defines a femoral channel guide that locates a broach on the femur to form the femoral channel at a known angular orientation relative to the anterior, distal, and posterior femoral faces such that the gusset and anterior, distal, and inner posterior femoral faces of the artificial femoral component align and mate with the corresponding features on the femur; and defines a set of datums (e.g., planar faces) that mate to the anterior, distal, and/or posterior femoral faces and that locate the femoral channel guide relative to these femoral faces according to the position of the gusset relative to the distal, posterior, and anterior inner faces of the artificial femoral component.

In this variation, the angular position of the sixth guide unit about the longitudinal axis of the femur is thus controlled by the posterior femoral face, and the angular position of the sixth guide unit about the sagittal and frontal axes of the femur is similarly controlled by the distal femoral face. The surgeon may therefore align the sixth guide unit to a lateral position of a trial femoral component (described below)—on the distal femoral face—that balances tensions on the medial ligament and the lateral ligament over the range of the motion of the knee.

4.7 Seventh Guide Unit: Tibial Boring Guide

In one variation, the system 100 additionally or alternatively includes a seventh guide unit that: defines a tibial boring guide that locates a reamer on the tibia to form the tibial bore at a known orientation relative to the proximal tibial face such that the post and inner proximal tibial face 191 of the artificial tibial component 190 align to and mate with the corresponding tibial bore and proximal tibial face of the tibia; and defines a set of datums (e.g., a planar face) that mate to the proximal tibial face and that locate the tibial boring guide relative to the proximal tibial face according to the position and orientation of the post relative to the inner proximal tibial face 191 of the artificial tibial component 190.

In this variation, the angular position of the seventh guide unit about the sagittal and frontal axes of the tibia is thus controlled by the proximal tibial face. The surgeon may therefore align the seventh guide unit to the lateral and sagittal positions of a trial tibial component (described below)—on the proximal tibial face—that balances tensions on the medial ligament and the lateral ligament over the range of the motion of the knee.

4.8 Planar/Non-Planar Cuts

As described above, the guide units can define planar cut guides configured to guide surgical tools along linear cut paths for form planar boney cuts to mate with planar surfaces of artificial components. Additionally or alternatively, the guide units can define non-planar or non-parallel cut guides configured to guide surgical tools along non-linear or non-parallel cut paths for form non-planar (or "native") boney cuts to mate with non-planar surfaces of artificial components.

5. Artificial Components

As shown in FIG. 1, the artificial tibial component 190 includes: a tibial plate; an inner proximal tibial face 191 that mates to the proximal tibial face; and a stem 193 extending from the inner proximal tibial face 191 and configured to insert into a tibial bore.

The artificial femoral component includes: a femoral plate configured to mate with and run along the tibial plate; an inner distal femoral face 195 mates to the distal femoral face; an inner posterior femoral face 196 mates to the posterior femoral face; an anterior inner face mates to the anterior femoral face; a gusset extending rearward from the inner faces and configured to mate with a distal femoral channel cut into the distal end of the femur to (over) constrain the artificial component in rotation about the longitudinal axis of the femur; and interior chamfer faces between the distal, posterior, and anterior inner faces.

In one example: the inner distal femoral face 195 of the artificial femoral component is parallel to the inner proximal tibial face 191 of the artificial tibial component 190 when the artificial knee is located in extension; the inner posterior femoral face 196 is perpendicular to the inner distal femoral face 195; and the anterior inner face is perpendicular to the inner distal femoral face 195 and parallel to the inner posterior femoral face 196.

5.1 Artificial Component and Guide Relationships

Generally, geometries of the set of guides correspond to the geometries of the artificial components, as shown in FIGS. 1 and 2.

In particular, when their datums are mated, the first and second guide units 101, 102, define the proximal tibial cut guide 130 and the distal femoral cut guide 140, respectively, offset by a distance and orientation corresponding to the offset distance and orientation between the inner proximal tibial face 191 of the artificial tibial component 190 and the inner distal femoral face 195 of the artificial femoral component when in extension. The third guide unit 103 defines a femoral side 154 offset from its tibial side 153 by an offset distance and orientation that correspond to the known offset distance and orientation between the inner proximal tibial face 191 of the artificial tibial component 190 and the inner distal femoral face 195 of the artificial femoral component when occupying the intermediate position. Similarly, the third guide unit 103 defines the posterior femoral cut guide 160 offset from the femoral side 154 by an offset distance and orientation that corresponds to the known offset distance and orientation between the inner distal femoral face 195 of the artificial femoral component and the inner posterior femoral face 196 of the artificial femoral component when occupying the intermediate position.

5.2 Trial Components

In one variation, the system 100 also includes: a trial tibial component defining an internal and external geometry matched to the artificial tibial component 190, less a stem; and a trial femoral component defining an internal and external geometry matched to the artificial femoral component, less an anterior section of the artificial femoral component configured to mate with an anterior femoral face, less the gusset of the artificial femoral component configured to mate with a distal femoral channel, and less internal chamfers of the artificial femoral component.

In this variation, the trial tibial component and/or the trial femoral components can also include a medial recess and a lateral recess (i.e., near their medial and lateral sides of these trial components) configured to receive the tension tool 105 or other force sensor, thereby enabling the surgeon to: insert the tension tool 105 or other force sensor into these recesses once these trial tibial and femoral components are located on the patient; traverse the knee through a range of motion; and monitor the tension across the medial ligament and the lateral ligament over this range of motion via the tension tool 105, which may predict the tension across the medial ligament and the lateral ligament over this range of motion once the artificial tibial and femoral components are fully implanted in the patient.

The surgeon may therefore locate the trial tibial component and trial femoral component on the patient's knee following the third stage of the surgery and insert the tension tool 105 or other force sensor between these trial components to validate tension across the medial ligament and the lateral ligament before performing the anterior femoral cut.

5.3 Trial Component and Guide Relationships

In the foregoing variation, the trial femoral component can define a set of (e.g., two) pin boring guides configured to locate a drill at positions matched to pins extending from the sixth guide unit (or matched to pin receivers defined by the sixth guide unit). After confirming location of the trial femoral component on the femur, the surgeon may: drill into the femur at these pin boring guides to create a set of locating holes in the femur (e.g., at the distal femoral face); and then insert pins extending from the sixth guide unit into these two bores to locate and fully constrain the sixth guide unit at a position on the femur that places the femoral channel guide in a lateral position on the femur that produces a distal femoral channel at a lateral position on the femur that mates with the gusset of the artificial femoral component to locate the artificial femoral component at the same position on the femur as the trial femoral component confirmed by the surgeon as producing balanced tension on the medial ligament and the lateral ligament over the range of motion of the knee.

Similarly, in this variation, the trial tibial component can define a set of (e.g., two) pin boring guides configured to locate a drill at positions matched to pins extending from the seventh guide unit (or matched to pin receivers defined by the seventh guide unit). Therefore, after confirming location of the trial tibial component on the tibia, the surgeon may: drill into the tibia at these pin boring guides to create a set of locating holes in the tibia (e.g., at the proximal tibial face); and then insert pins extending from the seventh guide unit into these two bores to locate and fully constrain the seventh guide unit at a position on the tibia that places the tibial boring guide in a lateral and sagittal position on the tibia that produces a tibial bore at a lateral and sagittal position on the tibia that receives the stem 193 of the artificial tibial component 190 to locate the artificial tibial component 190 at the same lateral and sagittal position on the tibia as the trial tibial component confirmed by the surgeon as producing balanced tension on the medial ligament and the lateral ligament over the range of motion of the knee.

In another variation, the trial femoral component and the sixth guide unit include like datums configured to mate with complementary datums on a femoral jig affixed to the femur during the surgery. The trial tibial component and the seventh guide unit similarly include like datums configured to mate with complementary datums on a tibial jig affixed to the tibia during the surgery. In this variation, the surgeon may affix the femoral jig to the femur and to the trial femoral component via their complementary datums and affix the tibial jig to the tibia and to the trial tibial component via their complementary datums. The surgeon may then: test tensions across the medial ligament and the lateral ligament over the range of motion of the knee with the trial femoral and tibial components located by these jigs; and adjust the lateral position of the trial femoral component on the femur via adjustment features on the femoral jig and adjust the lateral position, sagittal position, and longitudinal angular position of the trial tibial component on the femur via adjustment features on the tibial jig until the tensions on the medial ligament and the lateral ligament are balanced. Then surgeon may then: remove the trial femoral and tibial components from their jigs; mate the sixth and seventh guide units to the complementary datums on the femoral and tibial jigs, respectively; broach the distal femoral channel via the sixth guide unit; ream the tibial bore via the seventh guide unit; remove the guide and jigs; and install the artificial femoral and tibial components.

5.4 Artificial Component Selection

In one variation, the system 100 includes multiple artificial and trial tibial and femoral component groups of different sizes, integrated varus angles, and/or integrated valgus angles, etc. The surgeon may therefore select a particular group of guides, artificial components, and trial components matched to the patient's size and to the surgeon's preferences for final varus/valgus angle of the patient's knee, etc.

6. Surgical Process

After opening the patient's knee to expose the patient's femur and tibia, the surgeon may: remove osteophytes from the femur and tibia; and perform releases to balance the varus/valgus position of the knee if outside of a target range or the surgeon's preferences or surgical plan (e.g., standard releases for traditional coronal alignment, deep medial ligament release for a varus knee).

6.1 Ligament Tension Measurement

The surgeon may then: insert the internal jaws of a first instance of the tension tool 105 (or a first load cell pad) between the medial femoral condyle and the medial side of the tibia; insert the internal jaws of a second instance of the tension tool 105 (or a second load cell pad) between the lateral femoral condyle and the lateral side of the tibia; traverse the knee through its range of motion; and record nominal medial and lateral tensions measured by the first and second instances of the tension tool 105 (or load cells) over this range of motion or at target positions within the range of motion (e.g., extension, flexion, and an intermediate position, such as 60° from extension).

The surgeon may then specify target medial ligament and lateral ligament tensions over this range of motion or at these target positions within the range of motion, such as identical to these nominal medial and lateral tensions or deviating from these nominal medial and lateral tensions in order to achieve different post-operative articulation of the knee.

6.2 First Stage Proximal Tibial Cut

During a first stage of the surgery, the surgeon may: set the knee in extension; locate the first guide unit 101 over the tibial condyle; pin the first guide unit 101 to the tibia; and perform a proximal tibial cut by passing a blade (e.g., a reciprocating saw) through the proximal tibial cut guide 130, thereby forming the proximal tibial face on the tibia, that subsequently constrains the artificial tibial component 190 in longitudinal translation on the tibia, as shown in FIG. 4.

6.3 Second Stage: Distal Femoral Cut

During a second stage of the surgery, the surgeon may: insert the internal jaws of the first instance of the tension tool 105 between the femoral condyle and the proximal face of the tibia near the medial side of the tibia; insert the internal jaws of the second instance of the tension tool 105 between the femoral condyle and the proximal face of the tibia near the lateral side of the patient's knee, as shown in FIG. 4; adjust the first tension tool 105 to set the tension on the medial ligament to a target medial tension in extension; and adjust the second tension tool 105 to set the tension on the lateral ligament to a target lateral tension in extension.

Once the target extension tensions on the medial ligament and the lateral ligament are set via the first and second instances of the tension tool 105, the surgeon may plate the second guide unit 102 on the femur, bring the datums of the first and second guide units 101, 102 into contact to locate the second guide unit 102 relative to the first guide unit 101, and fasten (or "pin") the second guide unit 102 to the femur, thereby locating the distal femoral cut guide 140 defined by the second guide unit 102 relative to the proximal tibial face previously cut according to the proximal tibial cut guide 130.

The surgeon may then perform a distal femoral cut by passing a saw through the distal femoral cut guide 140. The resulting distal femoral face is thus located relative to the proximal tibial face—with the tension on the medial ligament and the lateral ligament balanced and at their target extension tensions—according to an offset between the inner distal femoral face 195 of the artificial femoral component and the inner proximal tibial face 191 of the artificial tibial component 190 when the knee is in extension.

More specifically, the distal femoral face constrains the artificial femoral component in longitudinal translation, rotation about the frontal axis, and rotation about the sagittal axis of the femur. The proximal tibial face similarly constrains the artificial tibial component 190 in longitudinal translation, rotation about the frontal axis, and rotation about the sagittal axis of the tibia. Therefore, once the proximal tibial cut is made by the surgeon and with the knee remaining in extension and the first guide unit 101 remaining fixed to the tibia, the first guide unit 101 locates the second guide unit 102 on the femur, thereby locating the distal femoral cut guide 140 at a known distance and orientation relative to the proximal tibial face. This known distance and orientation between the proximal tibial face and the distal femoral cut guide 140—and thus the resulting distal femoral face cut along the distal femoral cut guide 140 during the second stage of the surgery—is based on the distance and orientation between the inner proximal tibial face 191 of the artificial tibial component 190 and the distal femoral face of the artificial femoral component in extension. Thus, because the second guide unit 102 is located on the femur relative to the first guide unit 101 when the medial ligament and the lateral ligament are set at corresponding target extension tensions, the proximal tibial face and the distal femoral face—cut along the proximal tibial cut guide 130 and the distal femoral cut guide 140, respectively—are located at known relative offset distances and orientations matched to the artificial tibial and femoral components. Therefore, when the inner proximal tibial face 191 of the artificial tibial component 190 is located on the proximal tibial face, when the distal femoral face of the artificial femoral component is located on the distal femoral face, and when the knee is placed in extension, the medial ligament and the lateral ligament may return to (or very near) their target extension tensions.

6.4 Third Stage: Posterior Femoral Cut

The surgeon may then: articulate the knee to an intermediate position, such as 60° from extension; loosely place the tibial-side of the third guide unit 103 on the proximal tibial face; loosely place the femoral-side of the third guide unit 103 on the distal femoral face; insert the internal jaws of the first instance of the tension tool 105 between the femoral condyle and the proximal face of the tibia near the medial side of the tibia; insert the internal jaws of the second instance of the tension tool 105 between the femoral condyle and the proximal face of the tibia near the lateral side of the patient's knee; adjust the first tension tool 105 to set the tension on the medial ligament to a target medial tension in the intermediate position; and adjust the second tension tool 105 to set the tension on the lateral ligament to a target lateral tension in the intermediate position.

Once the target intermediate tensions are set on the medial ligament and the lateral ligament via the first and second instances of the tension tool 105, the surgeon may float the third guide unit 103 into space between the femur and tibia to confirm contact: between the tibial-side of the third guide unit 103 and the proximal tibial face; and between the femoral-side of the third guide unit 103 and the distal femoral face. The surgeon may then pin the third guide unit 103 to the femur (e.g., to the distal femoral face), as shown in FIG. 2.

In particular, tensioning the medial ligament and the lateral ligament in the intermediate position as described above spreads the proximal tibial face and distal end of the femur on the medial side of the patient's knee to a medial gap that yields the target tension on the medial ligament. This action similarly spreads the proximal tibial face and distal end of the femur on the lateral side of the knee to a lateral gap that yields the target tension on the lateral ligament (which may differ from the medial gap). However, the third guide unit 103 defines a wedge geometry including: a tibial side 153 that mates against the (approximately) planar proximal tibial face; and a femoral side 154 that mates against the (approximately) planar distal femoral face. The surgeon may therefore drive the third guide unit 103 into best contact with the proximal tibial face and distal femoral face while the medial ligament and lateral ligament are held in their target intermediate tensions. If the medial and lateral gaps are identical, the proximal tibial and distal femoral faces may constrain the third guide unit 103 at an angle of approximately 0° about the mechanical axis of the femur. Conversely, if the medial gap is larger than the lateral gap, the third guide unit 103 may be angularly offset in a positive direction about the mechanical axis of the femur when the third guide unit 103 is constrained against the proximal tibial and distal femoral faces such that the third guide fills the larger medial gap; and vice versa.

Once the surgeon pins the third guide unit 103 to the femur, the surgeon may bring the knee to flexion. (In the implementation described above in which the third guide unit 103 includes a secondary element defining the posterior femoral cut guide 160, the surgeon may then install the secondary element on the third guide unit 103 with the knee now in flexion.) The surgeon may then perform the posterior femoral cut by passing a saw through the posterior femoral cut guide 160 to complete this third step of the surgery.

Generally, the posterior femoral face constrains the artificial femoral component in translation parallel to the sagittal axis of the femur, constrains the artificial femoral component in rotation about the longitudinal axis of the femur, and (over)constrains the artificial femoral component in rotation about the frontal axis of the femur. The third guide unit 103 also defines the femoral side 154 offset from the tibial side 153 by an offset distance and orientation that corresponds to the known offset distance and orientation between the inner proximal tibial face 191 of the artificial tibial component 190 and the inner distal femoral face 195 of the artificial femoral component when occupying the intermediate position. The third guide unit 103 similarly defines the posterior femoral cut guide 160 offset from the femoral side 154 by an offset distance and orientation that corresponds to the known offset distance and orientation between the inner distal femoral face 195 of the artificial femoral component and the inner posterior femoral face 196 of the artificial femoral component when occupying the intermediate position. Because the third guide unit 103 is pinned to the femur once the tibial and femoral sides 153, 154 of the third guide unit 103 are brought into contact with the proximal tibial face and the distal femoral face while the medial ligament and the lateral ligament are set at corresponding target intermediate-position tensions, the posterior femoral face is located at the known offset distance and orientation relative to the distal femoral face matched to the artificial tibial and femoral components. Therefore, when the inner proximal tibial face 191 of the artificial tibial component 190 is located on the proximal tibial face, when the distal femoral face of the artificial femoral component is located on the distal femoral face, when the inner posterior femoral face 196 of the artificial femoral component is located on the posterior femoral face, and when the knee is placed in the intermediate position, the medial ligament and the lateral ligament may return to (or very near) their target intermediate tensions.

6.5 Fourth Stage: Conforming Bearing for Artificial Tibial Component Placement

As described below, the surgeon may then: place or finally install the artificial femoral component on the femur (i.e., in contact with and located by the distal and posterior femoral faces), such as at a surgeon-elected lateral-medial position approximately centered along a longitudinal axis of the femur or tibia; locate a conforming bearing 170—that approximates the thickness and nominal geometry of the artificial tibia component, excluding a stem 193—between the resected proximal tibial face and the artificial femoral component; move the knee through its range of motion to enable the conforming bearing 170 to slide over the resected proximal tibial face and find a balanced position that balances and minimize tensions on the medial and lateral ligaments over the range of motion of the knee; ream the tibia for the stem 193 of the artificial tibial component 190 according to the balanced position of the conforming bearing 170; and finally install the artificial tibial component 190 on the tibia.

Accordingly, because the geometry of the conforming bearing 170 approximates the geometry of the artificial tibial component 190—less the stem 193 of the artificial tibial component 190—and references a longitudinal cut through the tibia to locate the stem 193 of the artificial tibial component 190, a) tensions across the medial and lateral ligaments over the range of motion of the knee when the artificial femoral component and the conforming bearing 170 are installed in the knee may approximate b) tensions across the medial and lateral ligaments over the range of motion of the knee when the artificial femoral component and the artificial tibial component 190 are installed in the knee, all without necessitating further ligament tension measurements, ligament release, or component placement approximations or tests, etc.

6.6 Trial Components

In one variation, the surgeon may additionally or alternatively: place the trial tibial component on the proximal tibial face; place the trial femoral component on the distal and posterior femoral faces; move the knee through range of motion; and measure the tension on the medial ligament and lateral ligament through the range of motion of the knee, such as described above.

If the medial ligament is tight and the lateral ligament is loose(r) throughout this range of motion, the surgeon may further resect the medial side of proximal tibial face, which may produce rotation of the trial tibial component (and therefore the resulting artificial tibial component 190) about the sagittal axis of the tibia, thereby: reducing the distance between the medial side of the proximal tibial face and the distal femoral face in both flexion and extension thus reducing tension on the medial ligament in both flexion and extension; and maintaining the distance between the lateral side of the proximal tibial face and the distal femoral face in both flexion and extension and thus preserving tension on the lateral ligament in both flexion and extension.

If the medial ligament is tight and the lateral ligament is loose in flexion but balanced in extension, the surgeon may further resect the medial side of the posterior femoral face, which may produce rotation of the trial femoral component (and therefore the resulting artificial femoral component) about the longitudinal axis of the femur, thereby: reducing the distance between the medial side of the posterior femoral face and the proximal tibial face in flexion and thus reducing tension on the medial ligament in flexion; maintaining the distance between the lateral side of the posterior femoral face and the proximal tibial face in flexion and thus preserving tension on the lateral ligament in flexion; and maintaining the distance between the distal femoral face and the proximal tibial face in extension and thus preserving tension on the medial ligament and lateral ligament in extension.

If the medial ligament is tight and the lateral ligament is loose in extension but balanced in flexion, the surgeon may further resect the medial side of the distal femoral face, which may produce rotation of the trial femoral component (and therefore the resulting artificial femoral component) about the sagittal axis of the femur, thereby: reducing the distance between the medial side of the distal femoral face and the proximal tibial face in extension and thus reducing tension on the medial ligament in extension; maintaining the distance between the lateral side of the distal femoral face and the proximal tibial face in extension and thus preserving tension on the lateral ligament in extension; and maintaining the distance between the posterior femoral face and the proximal tibial face in flexion and thus preserving tension on the medial ligament and lateral ligament in flexion.

Therefore, because the first, second, and third guide units 101, 102, 103 link the proximal tibial, distal femoral, and posterior femoral cuts according to the geometries of the trial (and artificial) femoral and tibial components: the number and complexity of actions for balancing the medial ligament and lateral ligament following resection of the proximal, distal, and posterior faces of the tibia and femur are reduced; and specific actions (i.e., further bony cuts) of particular magnitudes yield specific results of predictable magnitudes.

6.6.1 Remaining Stages

Once tensions on the medial ligament and the lateral ligament over the range of motion of the knee are verified following the third stage of the surgery, the surgeon may: mark locations of the trial tibial and femoral components on the tibia and femur, respectively; place locating pins through these trial tibial and femoral components into the tibia and femur, respectively; or set tibial and femoral jigs in contact with these trial tibial and femoral components; or otherwise record the positions of these trial tibial and femoral components—in this balanced positions—on the patient's tibia and femur.

The surgeon may then implement methods and techniques described above to: locate the fourth guide unit in contact with the distal and posterior faces on the femur; perform the anterior femoral cut by passing a saw through the anterior femoral cut guide defined by the fourth guide unit; locate the fifth guide unit on the femur; perform the femoral chamfer cuts by passing a saw through the chamfer cut guides defined by the fifth guide unit; locate the sixth guide unit in contact with the distal, posterior, and/or anterior faces on the femur and aligned to the recorded position of the trial femoral component; perform the femoral channel cut by passing a broach through the femoral channel cut guide defined by the sixth guide unit; locate the seventh guide unit in contact with the proximal face on the tibia and aligned to the recorded position of the trial tibial component; and perform the tibia bore cut by passing a reamer through the tibia boring guide defined by the seventh guide unit.

6.7 Surgery Completion

The surgeon may then: remove all guides from the patient; install the artificial tibial and femoral components in the patient; verify tensions on the medial ligament and the lateral ligament over the range of motion of the knee; adjust final medial and lateral shim stacks and/or exchange an articulating space in the artificial tibia component in order to tune tensions on the medial ligament and the lateral ligament over the range of motion of the knee; and close the knee to complete the surgery.

7. Variation: Alignment and Cut Guides

One variation of the system 100 shown in FIGS. 5-8 includes: a proximal tibial alignment guide 110; a distal femoral alignment guide 120; a proximal tibial cut guide 130; a distal femoral cut guide 140; an intermediate femoral alignment guide 150; and a posterior femoral cut guide 160. The proximal tibial alignment guide 110: is configured to locate on a tibia of a leg in extension; defines a first set of tibial pin guides 111 configured to guide location of a first set of pins on the tibia; and defines a tibial reference surface 112 relative to the first set of tibial pin guides 111. The distal femoral alignment guide 120: is configured to locate on a femur of the leg in extension; is constrained relative to the proximal tibial alignment guide 110 by the tibial reference surface 112; and defines a first set of femoral pin guides 121, relative to the first set of tibial pin guides 111, configured to guide location of a second set of pins on the femur. The proximal tibial cut guide 130: is configured to locate on the tibia via the first set of pins; and defines a proximal tibial cut plane 132 for resecting a proximal structure of the tibia to form a resected proximal tibial face. The distal femoral cut guide 140: is configured to locate on the femur via the second set of pins; and defines a distal femoral cut plane 142, linearly offset from the proximal tibial cut plane 132, for resecting a distal structure of the femur to form a resected distal femoral face. The intermediate femoral alignment guide 150: is configured to insert between the tibia and the femur in partial flexion; includes a tibial side 153 configured to mate with the resected proximal tibial face; includes a femoral side 154 angularly offset from the tibial side 153 by an intermediate angle and configured to mate with the resected distal femoral face; and defines a second set of femoral pin guides 152, relative to the tibial side 153 and the femoral side 154, configured to guide location of a third set of pins on the femur. The posterior femoral cut guide 160: is configured to locate on the third set of pins; and defines a posterior femoral cut plane 162, angularly offset from the resected distal femoral face, for resecting a posterior structure of the tibia to form a resected distal femoral face.

A similar variation of the system 100 includes: a first alignment guide: a second alignment guide; a first cut guide; a second cut guide; a third alignment guide; a third cut guide; a conforming bearing 170; and a fourth cut guide. The first alignment guide: is configured to locate on a first bone of a joint in extension; defines a first set of pin guides configured to guide location of a first set of pins on the first bone; and defines a first reference surface relative to the first set of pin guides. The second alignment guide: is configured to locate on a second bone of the joint in extension; is constrained relative to the first alignment guide by the first reference surface; and defines a second set of pin guides, relative to the first set of pin guides, configured to guide location of a second set of pins on the second bone. The first cut guide: is configured to locate on the first bone via the first set of pins; and defines a first cut plane for resecting the first bone to form a first resected face on the first bone. The second cut guide: is configured to locate on the second bone via the second set of pins; and defines a second cut plane, linearly offset from the first cut plane, for resecting the second bone to form a second resected face on the second bone. The third alignment guide: is configured to insert between the first bone and the second bone in partial flexion; includes a first side configured to mate with the first resected face; includes a second side angularly offset from the first side by an intermediate angle and configured to mate with the second resected face; and defines a third set of pin guides, relative to the first side and the second side, configured to guide location of a third set of pins on the second bone. The third cut guide: is configured to locate on the third set of pins; and defines a posterior cut plane, angularly offset from the second resected face, for resecting a posterior structure of the first bone to form a third resected face on the second bone. The conforming bearing 170: defines a concave face configured to mesh with a convex face of a first artificial joint component installed over the first resected face of the first bone; defines a second face, opposite the convex face, configured to slide on the first resected face to seat in a ligament-balancing position on the first resected face as the first bone is moved over a range of motion relative to the second mode; and defines a fourth set of pin guides configured to guide location of a fourth set of pins on the first bone. The fourth cut guide: is configured to locate on the first bone via the fourth set of pins; and defines a longitudinal cut axis for boring the first bone to receive a stem 193 of the first artificial joint component.

7.1 Applications

Generally, in this variation, the system 100 can include: proximal tibial and distal femoral alignment guides 110, 120 that define pin guides for locating pins (e.g., straight, tapered, or eccentric pins) in relative positions on the tibia and femur; proximal tibial and distal femoral cut guides 130, 140 that are located on the tibia and femur via these pins and define proximal tibial and distal femoral cut planes 132, 142; a posterior femoral alignment guide that references the resected proximal tibial and distal femoral faces and defines pin guides for locating pins in a relative position on the femur; and a posterior femoral cut guide 160 that is located on the femur via these pins and defines a posterior femoral cut plane 162.

Accordingly, the system 100 can include a set of linked alignment and cut guide units that collectively define a sequence of linked pin locations that locate tibial and femoral cut guides that approximate known relative geometries of component-to-bone and component-to-component surfaces of artificial tibial and femoral components such that a) tensions on the medial and lateral ligaments of the knee when the set of linked alignment guides are pinned to the tibia and femur early in a surgery approximate b) the same tensions on the medial and lateral ligaments when the artificial tibial and femoral components are installed in the knee upon conclusion of the surgery.

More specifically, the proximal tibial, distal femoral, and posterior femoral alignment guides: link to reference surfaces defined by bony features in the knee, preceding alignment guides, and preceding bony cuts, respectively, exposed during the surgery; and define pin guides that guide (or "set") location of pins on the tibia and femur by a surgeon over a sequence of (e.g., three) surgical steps. The proximal tibial, distal femoral, and posterior femoral cut guides 130, 140, 160 define datums or other features that are located on the tibia and femur by these pins to define planar cut guides according to geometries of the inner proximal tibial, distal femoral, and posterior femoral faces of the artificial tibial and femoral components over a range of motion (e.g., in extension and partial-flexion at an intermediate angle) such that resection of the tibia and femur according to these planar cut guides produces resected tibial and femoral faces that accurately and repeatably locate the artificial tibial femoral components with ligament tensions that approximate (e.g., fall within 2% of) the ligament tensions present in the knee when the tibial, distal femoral, and posterior femoral alignment guides were first pinned to the tibial and femur.

As described below, the surgeon may tension (or "balance") the medial and lateral ligaments in the knee to target tensions (e.g., tight but not plastically deformed) before locating the proximal tibial, distal femoral, and posterior femoral alignment guides on the tibia and femur. Therefore, because geometries of the proximal tibial, distal femoral, and posterior femoral alignment and cut guides are linked to (i.e., prescribed by, approximate) the geometries of the artificial tibial and femoral components, these ligament tensions during placement of the proximal tibial, distal femoral, and posterior femoral alignment guides on the knee are replicated (e.g., to a tolerance of +/−2% of tensile force) when the artificial tibial and femoral components are finally installed in the knee and when the knee is located at the same extension-flexion positions.

7.2 Artificial Tibial and Femoral Components

Figure 5:
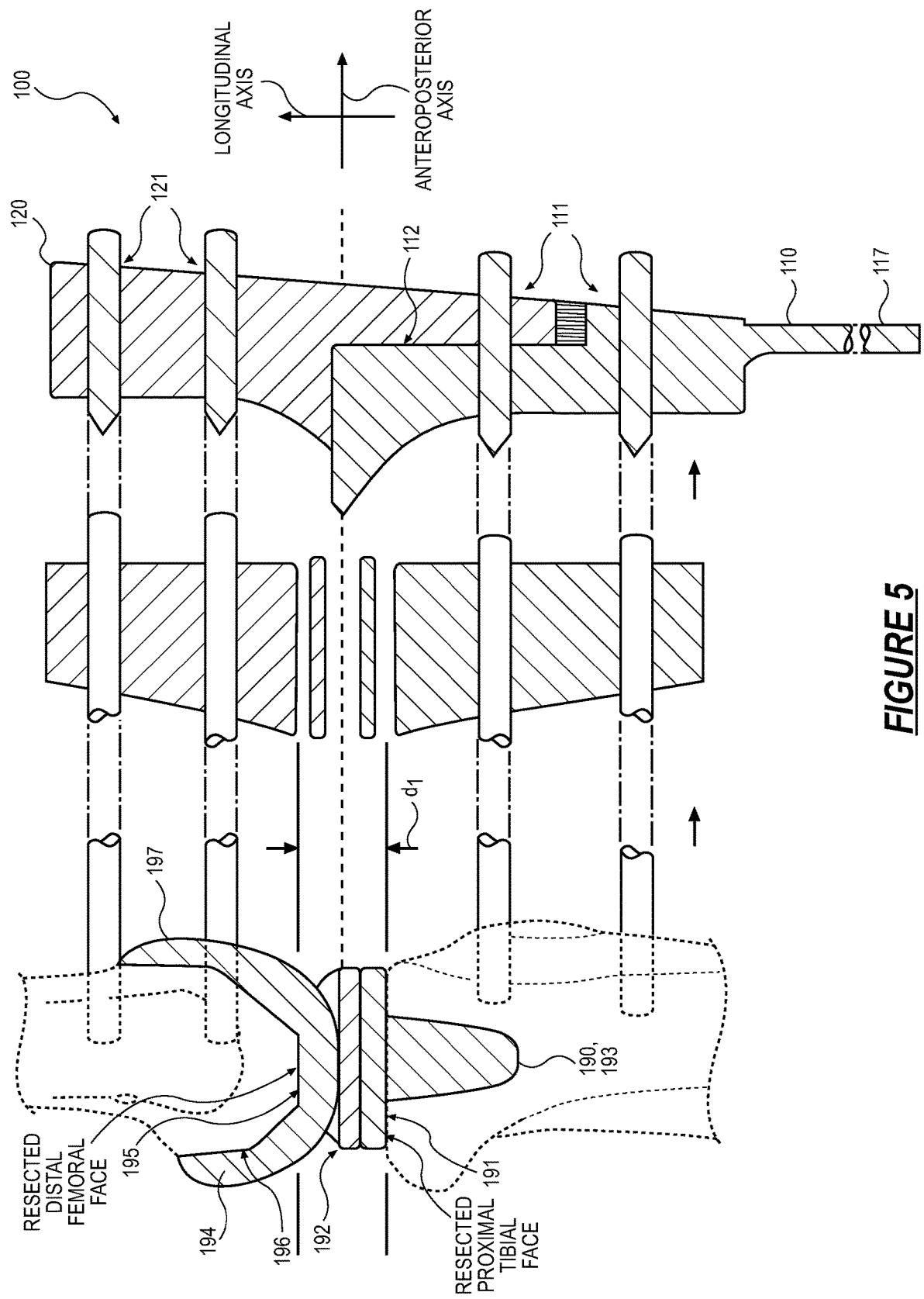
FIG. 5 is a schematic representation of one variation of the system.
Figure 7:
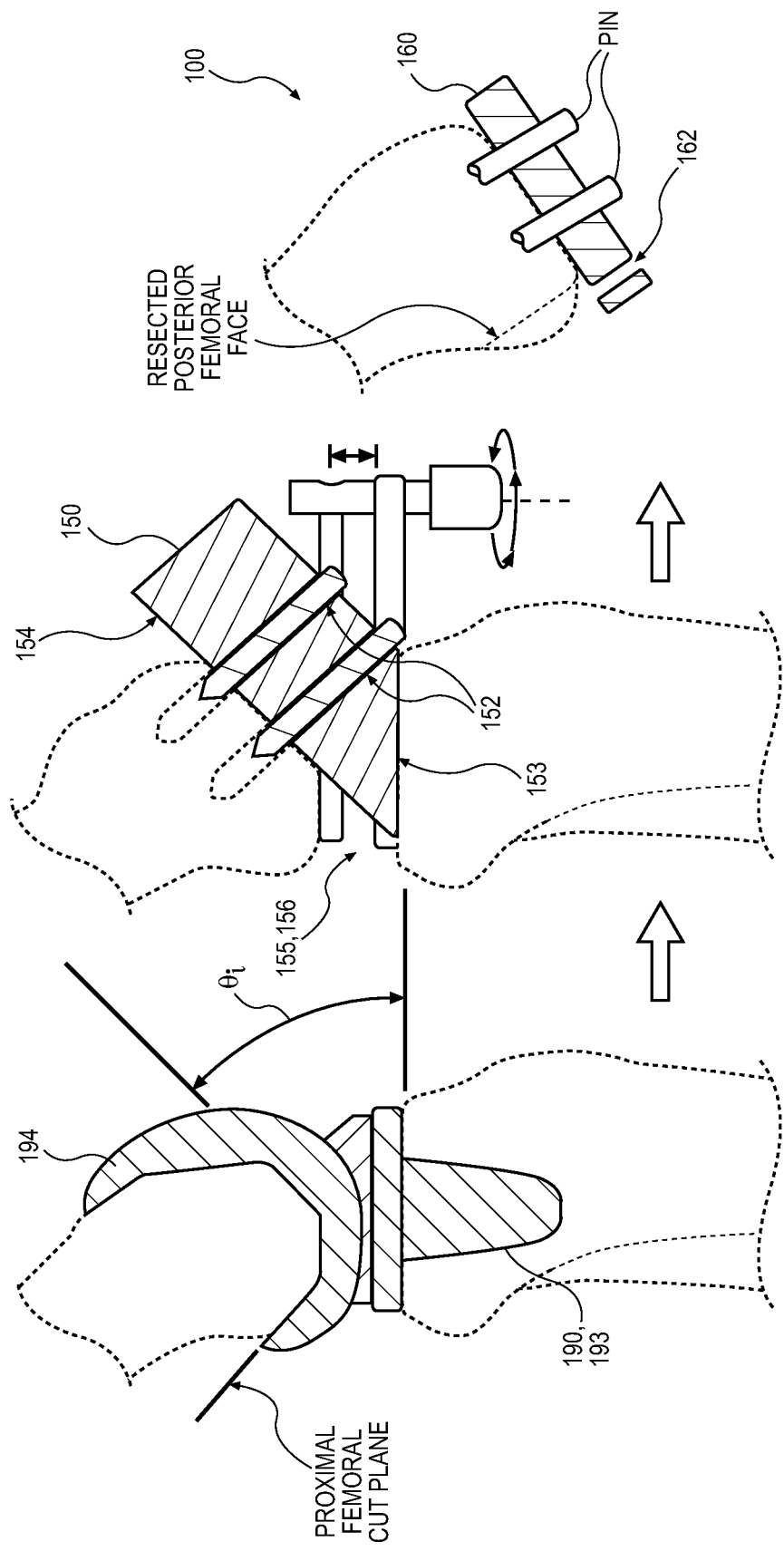
FIG. 7 is a schematic representation of one variation of the system.

In this variation, the system 100 can further include (or interface with) an artificial tibial component 190 and an artificial femoral component, as shown in FIGS. 5 and 7.

In one implementation, the artificial tibial component 190: defines an inner proximal tibial face 191 configured to mate with the resected proximal tibia face and constrained by the resected proximal tibia face in translation along a tibial longitudinal axis, in rotation about a tibial medial-lateral axis, and in rotation about a tibial anteroposterior axis; and defines a tibial mating surface 192. For example, the artificial tibial component 190 can include: a tibial plate defining the inner proximal tibial face 191 configured to seat on the resected proximal tibial face and including a stem 193 configured to insert into a longitudinal bore cut or reamed in the resected proximal tibial face; and a spacer (or a set of spacers of different height) located by the tibial plate and defining a concave tibial mating surface 192 configured to mate with the artificial femoral component.

In this implementation, the artificial femoral component: defines an inner distal femoral face 195 configured to mate with the resected distal femoral face and constrained by the resected distal femoral face in translation along a femoral longitudinal axis, in rotation about a femoral medial-lateral axis, and in rotation about a femoral anteroposterior axis; defines an inner posterior femoral face 196 configured to mate with the resected posterior femoral face and constrained by the resected posterior femoral face in translation along the femoral anteroposterior axis and in rotation about the femoral longitudinal axis; and defines a femoral mating surface 197 configured to mate with and slide (e.g., pivot, slip) along the tibial mating surface 192.

7.3 Proximal Tibial and Femoral Alignment and Cut Guides

Figure 6:
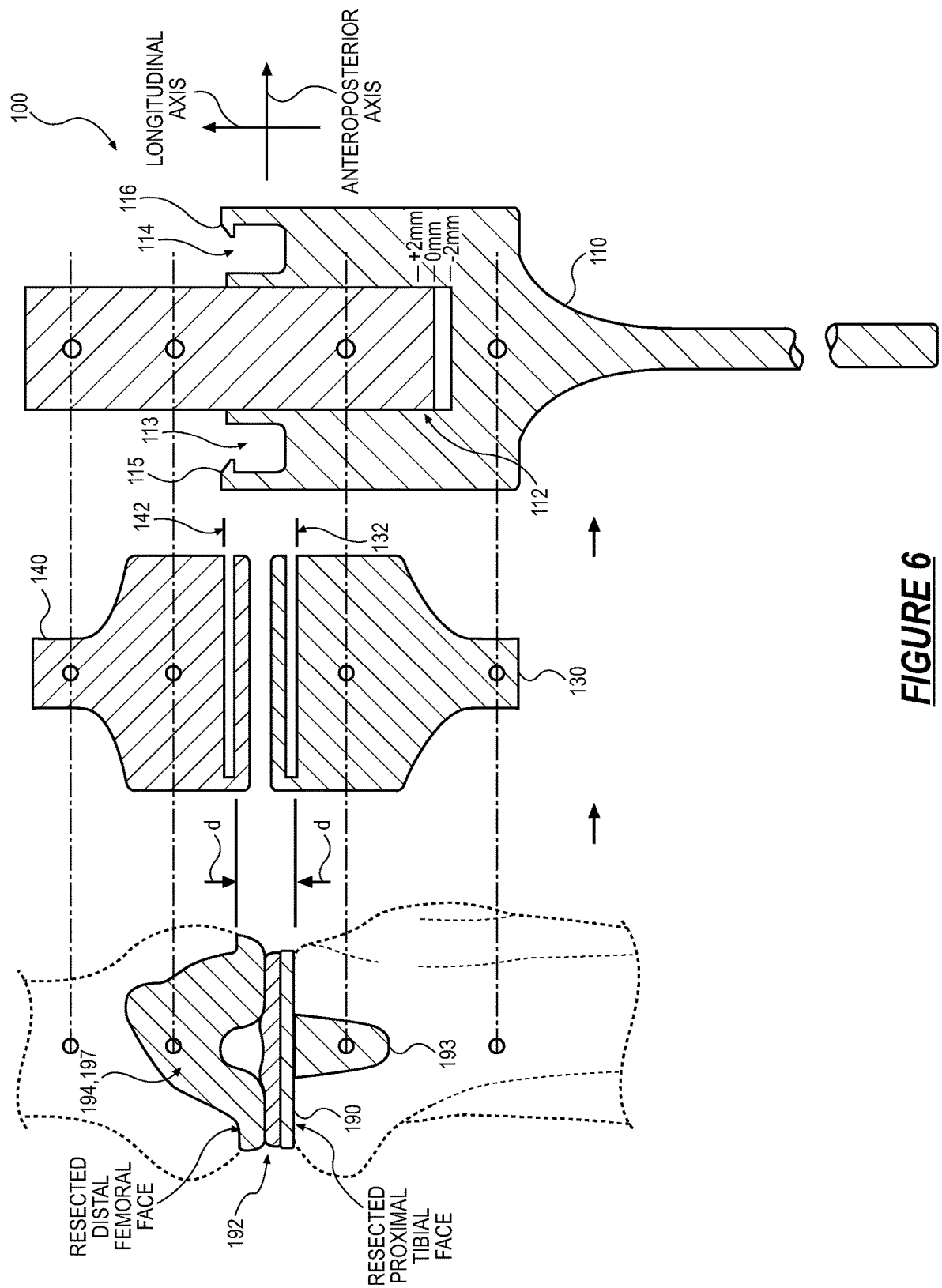
FIG. 6 is a schematic representation of one variation of the system.

In one implementation as shown in FIGS. 5 and 6, the proximal tibial alignment guide 110 is configured to locate on the tibia and the distal femoral alignment guide 120 is configured to locate on the femur: a) with the knee located in extension; b) the medial ligament tensioned to a target extension tension; and c) the lateral ligament tensioned to the target extension tension. In this implementation, the proximal tibial alignment guide 110 defines a tibial reference surface 112 (e.g., a planar surface, a channel, a set of kinematic datums) that locates the distal femoral alignment guide 120 such that the first set of pin guides is distally offset from the second set of pin guides by a first distance.

In this implementation, the proximal tibial cut guide 130: locates on the tibia via the first set of pins; and defines the proximal tibial cut plane 132 offset from the first set of pins by a second distance. Similarly, the distal femoral tibial cut guide: locates on the femur via the second set of pins; and defines the distal femoral cut plane 142 parallel to the proximal tibial cut plane 132 and offset from the first set of pins by a third distance.

In this implementation, a sum of the second distance, the third distance, and a target combined height of the artificial tibial component 190 and the artificial femoral component in extension (i.e., a distance from the inner proximal tibial face 191 of the artificial tibial component 190 to the inner distal femoral face 195 of the artificial femoral component) approximates the first distance such that the target extension tension on the medial ligament and the lateral ligament is inherently achieved when the artificial tibial component 190 and the artificial femoral component are installed in the knee and the knee is located in extension.

Furthermore, in this implementation, the proximal tibial alignment guide 110 can: define a m*edial window 113 configured to pass a medial tensioner (e.g., a first tension tool 105) that contacts a medial side of the proximal structure of the tibia (e.g., a medial tibial condyle) and a medial side of the distal structure of the femur (e.g., a medial femoral condyle) to tension the medial ligament of the knee (e.g., prior to location of the distal femoral alignment guide 120 on the femur); and similarly define a l*ateral window 114 configured to pass a lateral tensioner (e.g., a second tension tool 105) that contacts a lateral side of the proximal structure of the tibia (e.g., a lateral tibial condyle) and a lateral side of the distal structure of the femur (e.g., a lateral femoral condyle) to tension the lateral ligament of the knee (e.g., prior to location of the distal femoral alignment guide 120 on the femur). For example, the medial and l*ateral windows 113, 114 can include orifices and channels on the medial and lateral sides, respectively, of the proximal tibial alignment guide 110. Accordingly, the surgeon may: pin the proximal tibial alignment guide 110 on the tibia (e.g., with indicators on the proximal tibial alignment guide 110 pointing at medial and lateral junctions between the tibia and femur within the knee, as described below); insert medial and lateral tension tools 105 through the medial and l*ateral windows 113, 114 to tension the medial and lateral ligaments to target extension tensions; locate the distal femoral alignment guide 120 on the tibial reference surface 112 of the proximal tibial alignment guide 110; and then pin the distal femoral alignment guide 120 to the femur such that the relative locations of the proximal tibial and distal femoral alignment guides 110, 120 on the tibia and femur, respectively, represent the target tensions on the medial and lateral ligaments.

7.3.1 Distal Femoral Alignment Jig Location

Generally, the proximal tibial alignment guide 110 defines the first set of tibial pin guides 111 for drilling a first set of bores into the tibia to receive the first set of pins. The distal femoral alignment guide 120: mates with and is constrained by the tibial reference surface 112 (at least) in rotation about a medial-lateral axis of the proximal tibial alignment guide 110 and in rotation about an anteroposterior axis of the proximal tibial alignment guide 110; and defines the second set of tibial pin guides 172 for drilling a second set of bores into the femur, relative to the first set of bores, to receive the second set of pins.

In one implementation, the tibial reference surface 112 is configured to constrain the distal femoral alignment guide 120 in translation along a longitudinal axis of the proximal tibial alignment guide 110 such that proximal tibial and distal femoral cut guides 130, 140 cooperate to define parallel proximal tibial and distal femoral cut planes 132, 142 offset by a distance approximating (e.g., equal to; greater than to accommodate a tibial shim) a nominal distance between inner proximal tibial and distal femoral faces of the artificial tibial and femoral components in extension. Accordingly, the proximal tibial cut guide 130 is constrained on the tibia by the first set of pins: in rotation about a medial-lateral axis of the tibia; in rotation about an anteroposterior axis of the tibia; and in translation over a first range of linear distances along a longitudinal axis of the tibia according to a height of an artificial tibial component 190. The proximal tibial cut guide 130 is constrained on the femur by the second set of pins: in rotation about a medial-lateral axis of the femur; in rotation about an anteroposterior axis of the femur; and in translation over a second range of linear distances along a longitudinal axis of the femur according to a height of an artificial femoral component.

In another implementation, the tibial reference surface 112 is configured to constrain the distal femoral alignment guide 120 in translation along a longitudinal axis of the proximal tibial alignment guide 110 over a range of linear distances that are selectable by the surgeon according to a target combined height of an artificial tibial component 190 and an artificial femoral component in extension, such as to accommodate different tibial spacer or tibia shim heights.

7.3.2 Ankle Alignment Indicator

In one variation shown in FIGS. 5 and 6, the system 100 further includes an ankle alignment indicator 117: extending distally from the proximal tibial alignment guide 110; configured to indicate an angular offset about a tibial anteroposterior axis and a tibial medial-lateral axis between a mechanical axis of the tibia and the proximal tibial cut plane 132, defined by the proximal tibial cut guide 130 located on the tibia via the first set of pins, prior to placement of the proximal tibial cut guide 130 on the tibia and prior to resection of the proximal structure of the tibia; and configured to indicate an angular offset about a femoral anteroposterior axis and a femoral medial-lateral axis between the mechanical axis of the tibia and the distal femoral cut plane 142, defined by the distal femoral cut guide 140 located on the femur via the second set of pins, prior to placement of the distal femoral cut guide 140 on the femur and prior to resection of the distal structure of the femur, the distal femoral cut plane 142 parallel to and linearly offset from the proximal tibial cut plane 132.

Thus, in this variation, the surgeon may refer to the position of the ankle alignment indicator 117 relative to the patient's foot or ankle when setting the angular positions of the proximal tibial alignment guide 110 about anteroposterior and medial-lateral axes of the tibia.

7.3.3 Medial and Lateral Indicators

Additionally or alternatively, the proximal tibial alignment guide 110 can include: a medial indicator 115 configured for alignment with a medial interstice between a medial tibial plateau and a medial femoral condyle during location of the proximal tibial alignment guide 110 on the tibia; and a lateral indicator 116 configured for alignment with a lateral interstice between a lateral tibial plateau and a lateral femoral condyle during location of the proximal tibial alignment guide 110 on the tibia, as shown in FIGS. 5 and 7. In particular, the medial and lateral indicators 115, 116 can be linked to (i.e., represent, replicate) the known position of medial and lateral contact points of the artificial tibial and femoral components when assembled and located in extension.

Thus, in this variation, the surgeon may locate the proximal tibial alignment guide 110 on the tibia such that the medial and lateral indicators 115, 116 point at the medial and lateral contact points between the tibia and the femur in extension such that the location of the medial and lateral contact points of the artificial tibial and femoral components, when installed in the knee upon completion of the surgery, replicate the original medial and lateral contact points between the tibia and the femur in extension.

In one example, the proximal tibial alignment guide 110 defines the first set of tibial pin guides in longitudinally offset from the medial indicator 115 and the lateral indicator 116 by a first distance. The proximal tibial cut guide 130: locates on the tibia via the first set of pins; and defines the proximal tibial cut plane 132 longitudinally offset from the first set of pins by a second distance. A first sum of the second distal distance and an effective height of the artificial tibial component 190 in extension approximates the first distance. The distal femoral alignment guide 120: locates on the proximal tibial alignment guide 110 by the tibial reference surface 112; and defines the second set of femoral pin guides 152 longitudinally offset from the medial indicator 115 and the lateral indicator 116 by a third distance when located by the tibial reference surface 112. The distal femoral cut guide 140: locates on the femur via the second set of pins; and defines the distal femoral cut plane 142 longitudinally offset from the second set of pins by a fourth distance. Finally, a second sum of the fourth distal distance and an effective height of the artificial femoral component in extension approximates the third distance.

7.4 Intermediate Femoral Alignment and Cut Guides

In one implementation as shown in FIG. 6, the intermediate femoral alignment guide 150 defines a wedge geometry that forms the intermediate angle (e.g., between 55° and 65°) between the tibial side 153 and the femoral side 154 of the intermediate femoral alignment guide 150 such that the tibial side 153 mates with the resected proximal tibial face and the femoral side 154 mates with the resected distal femoral face when the knee is in partial flexion (e.g., between 55° and 65° from extension).

In particular, the proximal tibial alignment guide 110 is configured to locate on the tibia and the distal femoral alignment guide 120 is configured to locate on the femur with: a) the knee located in extension; b) the medial ligament tensioned to a target extension tension; and c) the lateral ligament tensioned to a target extension tension. The intermediate femoral alignment guide 150 is configured to seat against the resected proximal tibial face and the resected distal femoral face with: a) the knee located in partial flexion; b) the medial ligament tensioned to a target partial-flexion tension; and c) the lateral ligament tensioned to a target partial-flexion tension.

In one implementation, the intermediate femoral alignment guide 150: defines a second m*edial window 155 configured to pass a second medial tensioner that contacts a medial side of the resected proximal tibial face and a medial side of the resected distal femoral face to tension the medial ligament (e.g., prior to the tibial side 153 of the intermediate femoral alignment guide 150 seating on the resected proximal tibial face and the femoral side 154 of the intermediate femoral alignment guide 150 seating on the resected distal femoral face); and defines a second l*ateral window 156 configured to pass a second lateral tensioner that contacts a lateral side of the resected proximal tibial face and a lateral side of the resected distal femoral face to tension the lateral ligament (e.g., prior to the tibial side 153 of the intermediate femoral alignment guide 150 seating on the resected proximal tibial face and the femoral side 154 of the intermediate femoral alignment guide 150 seating on the resected distal femoral face).

For example, the medial and l*ateral windows 113, 114 can include orifices and channels on the medial and lateral sides, respectively, of the intermediate femoral alignment guide 150. Accordingly, the surgeon may: insert the intermediate femoral alignment guide 150 between the tibia and femur; approximately locate the knee in partial-flexion with the tibial and femoral sides 153, 154 of the intermediate femoral alignment guide 150 near or in contact with the resected proximal tibial and distal femoral faces; insert medial and lateral tension tools 105 through the medial and l*ateral windows 113, 114 to tension the medial and lateral ligaments to target partial-flexion tensions; press (or "drive") the tibial and femoral sides 153, 154 of the intermediate femoral alignment guide 150 into full contact with the resected proximal tibial and distal femoral faces; and then pin the intermediate femoral alignment guide 150 to the femur.

7.4.1 Intermediate Femoral Geometry

In this implementation, the intermediate femoral alignment guide 150 defines a nominal geometry between the tibial side 153 and the femoral side 154 that approximates a first target geometry between the inner proximal tibial face 191 of the artificial tibial component 190 and the inner distal femoral face 195 of the artificial femoral component when the artificial tibial component 190 and the artificial femoral component are assembled and form the intermediate angle. In this example, the posterior femoral cut guide 160 defines the posterior femoral cut plane 162 relative to the distal femoral face, when located on the femur via the third set of pins, according to a position of the inner posterior femoral face 196 of the artificial femoral component relative to the inner distal femoral face 195 of the artificial femoral component.

In one example, the intermediate femoral alignment guide 150 defines a nominal geometry between the tibial side 153 and the femoral side 154 that approximates a first target geometry between an inner proximal tibial face 191 of an artificial tibial component 190 and an inner distal femoral face 195 of an artificial femoral component when the artificial tibial component 190 and the artificial femoral component are assembled and form the intermediate angle. The intermediate femoral alignment guide 150 defines the second set of femoral pin guides 152 at a first offset from the tibial side 153 and the femoral side 154. The posterior femoral cut guide 160 defines the posterior femoral cut plane 162 at a second offset from the third set of pins when located on the femur. Thus, a sum of the first offset and the second offset approximates relative positions of the inner proximal tibial face 191 of the artificial tibial component 190, the inner distal femoral face 195 of the artificial femoral component, and an inner posterior femoral face 196 of the artificial femoral component when the artificial tibial component 190 and the artificial femoral component form the intermediate angle to produce the target partial-flexion tension on the medial ligament and the lateral ligament a) with the artificial tibial component 190 and the artificial femoral component installed in the knee and b) with the knee forming the intermediate angle.

7.5 System Geometry

In one example, the proximal tibial alignment guide 110 is configured to locate on the tibia and the distal femoral alignment guide 120 is configured to locate on the femur with: a) the knee located in extension; b) a medial ligament of a knee in the leg tensioned to a target extension tension; and c) a lateral ligament of the knee tensioned to a target extension tension. The tibial reference surface 112 locates the distal femoral alignment guide 120 with the first set of pin guides distally offset from the second set of pin guides by a first distance. The proximal tibial cut guide 130: locates on the tibia via the first set of pins; and defines the proximal tibial cut plane 132 offset from the first set of pins by a second distance. The distal femoral tibial cut guide: locates on the femur via the second set of pins; and defines the distal femoral cut plane 142 parallel to the proximal tibial cut plane 132 and offset from the first set of pins by a third distance. Thus, in this example, a first sum of the second distance, the third distance, and a target combined distance between an inner proximal tibial face 191 of an artificial tibial component 190 and an inner distal femoral face 195 of an artificial femoral component approximates the first distance to produce the target extension tension on the medial ligament and the lateral ligament with the artificial tibial component 190 and the artificial femoral component installed in the knee and with the knee in extension.

Furthermore, in this example, the intermediate femoral alignment guide 150 defines a nominal geometry between the tibial side 153 and the femoral side 154 that approximates a first target geometry between the inner proximal tibial face 191 of the artificial tibial component 190 and the inner distal femoral face 195 of the artificial femoral component when the artificial tibial component 190 and the artificial femoral component are assembled and form the intermediate angle. The intermediate femoral alignment guide 150 defines the second set of femoral pin guides 152 at a first offset from the tibial side 153 and the femoral side 154. The posterior femoral cut guide 160 defines the posterior femoral cut plane 162 at a second offset from the third set of pins when located on the femur. Thus, in this example, a second sum of the first offset and the second offset approximates relative positions of the inner proximal tibial face 191 of the artificial tibial component 190, the inner distal femoral face 195 of the artificial femoral component, and the inner posterior femoral face 196 of the artificial femoral component when the artificial tibial component 190 and the artificial femoral component are assembled and form the intermediate angle to produce the target partial-flexion tension on the medial ligament and the lateral ligament with the artificial tibial component 190 and the artificial femoral component installed in the knee and with the knee forming the intermediate angle.

7.6 Conforming Bearing

Figure 8:
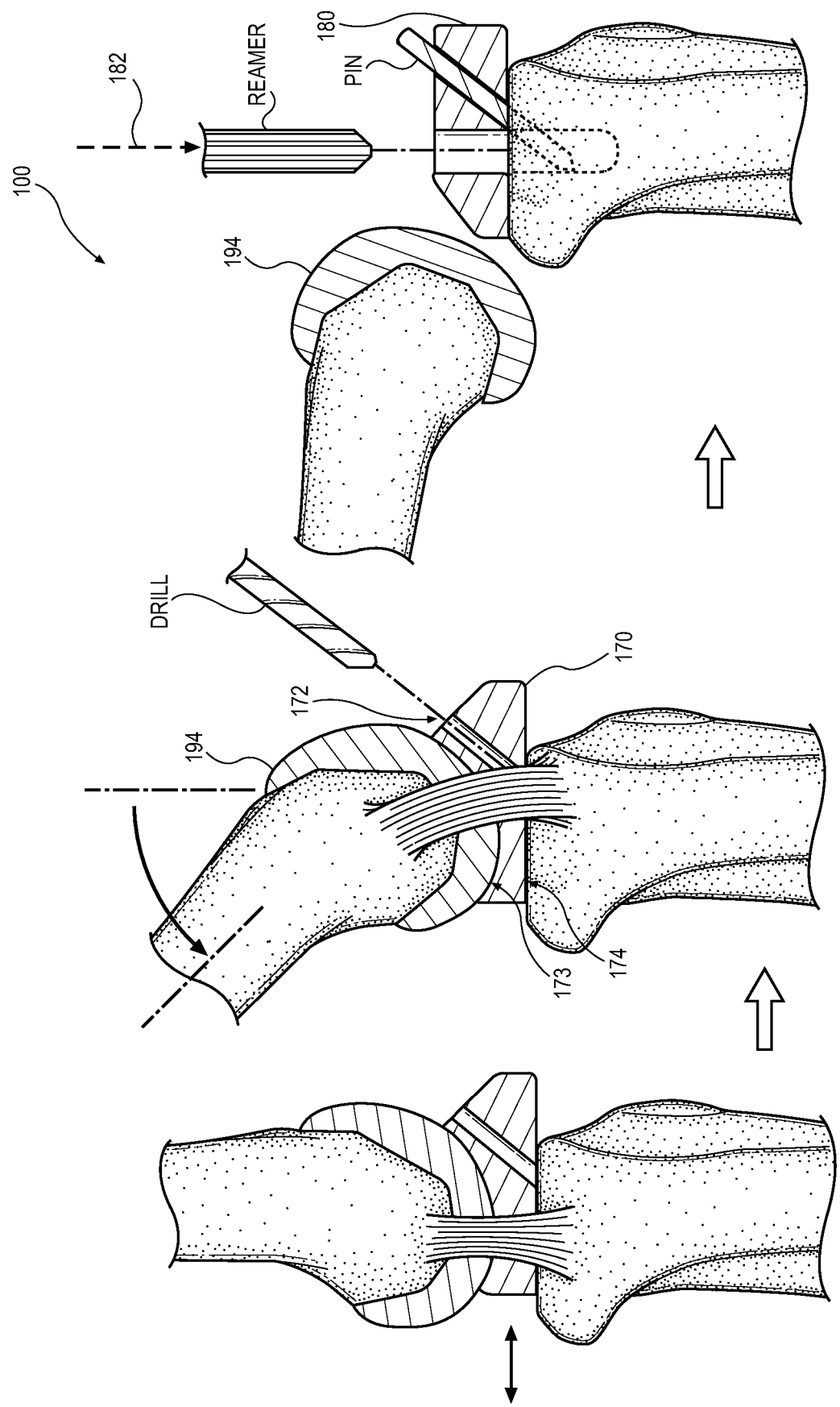
FIG. 8 is a schematic representation of one variation of the system.

In one variation as shown in FIG. 8, the system 100 further includes a conforming bearing 170: defining a proximal concave face 173 configured to mesh with a distal convex face of an artificial femoral component installed over the resected distal femoral face; defining a distal face 174 configured to slide on the resected proximal tibial face to seat in a ligament-balancing position on the resected proximal tibial face as the tibia is moved over a range of motion relative to the femur, a medial ligament and a lateral ligament in the leg approaching minimum peak tensions over the range of motion with the conforming bearing 170 occupying the ligament-balancing position on the resected proximal tibial face; and defining a second set of tibial pin guides 172 configured to guide location of a fourth set of pins on the tibia. In this variation, the system 100 also includes a longitudinal tibial cut guide 180: configured to locate on the tibia via the fourth set of pins; and defining a longitudinal tibial cut axis 182 for boring the tibia to receive a stem 193 of an artificial tibial component 190.

In particular, the conforming bearing 170: defines a nominal geometry that approximates a target geometry of a proximal section of an artificial tibial component 190 configured to seat over the resected proximal tibial face; and defines the second set of tibial pin guides 172 at a first offset (e.g., known linear offsets along medial-lateral and anteroposterior axes of the tibia) from the proximal concave face 173. The longitudinal tibial cut guide 180 defines the longitudinal tibial cut axis 182 at a second offset (e.g., known linear offsets along the medial-lateral and anteroposterior axes of the tibia) from the fourth set of pins. Accordingly, a sum of the first offset and the second offset approximates a position (e.g., an axis) of a stem 193 of the artificial tibial component 190 relative to the proximal section of the artificial tibial component 190 to locate the artificial tibial component 190 in the ligament-balancing position on the tibia over the range of motion of the knee.

For example, a first vector in three-dimensional space may represent the first offset: from the second set of tibial pin guides 172; to a contact point on the proximal concave face 173 of the conforming bearing 170 that mates with the artificial femoral component in extension. A second vector in three-dimensional space may represent the second offset: from features on the longitudinal tibial cut guide 180 that locate on the second set of tibial pin guides 172; to the longitudinal tibial cut axis 182. Accordingly, a sum of the first offset and the second offset approximates a three-dimensional offset: from an axis of a stem 193 of the artificial tibial component 190; to a contact point on the proximal section of the artificial tibial component 190 that mates with the artificial femoral component in extension, thereby preserving medial and lateral ligament tension from the conforming bearing 170 occupying the ligament-balancing position on the tibia to final installation of the artificial tibial component 190 in the knee.

In one implementation, the conforming bearing 170 includes a polyethylene body with a smooth distal section such that the conforming bearing 170 can freely slide across the resected proximal tibial face as the surgeon sweeps the knee through its range of motion such that the conforming bearing 170 may find (or slide, slip into) the ligament-balancing position with minimal or no binding against the artificial femoral component. In particular, if the conforming bearing 170 is outside of the ligament-balancing position as the knee is articulated, the effective length of the artificial femoral component and the conforming bearing 170 may increase on one or both sides of the joint, thereby increasing tension on one or both medial and lateral ligaments in the joint. As the knee moves toward flexion, proportions of forces applied to the joint by the medial and lateral ligaments in the anteroposterior and medial-lateral directions increase. The resulting anteroposterior and medial-lateral force components may thus cause the conforming bearing 170 to translate in the anteroposterior and medial-lateral direction and rotation above the longitudinal tibial axis to find a new position that a) reduces the effective length of the artificial femoral component and the conforming bearing 170 and thus b) yields less tension in the medial and lateral ligaments.

The surgeon may therefore repeatedly move the knee through extension-flexion cycles to enable tensions on the medial and lateral ligaments to drive the conforming bearing 170 into the ligament-balancing position in which tensions on the medial and lateral ligaments are similar (or "balanced") at any position of the knee.

In this variation, the system 100 can also include a set of (flat) shims configured for insertion between the conforming bearing 170 and the resected proximal tibial face to enable the surgeon to increase nominal tensions on the medial and lateral ligaments during this process by inserting shims. Additionally or alternatively, the system 100 can include a set of conforming bearings 170 of different effective heights—matched to available artificial tibial component 190 heights—to enable the surgeon to tune nominal tensions on the medial and lateral ligaments during this process by exchanging conforming bearings 170.

Once the conforming bearing 170 enters the ligament-balancing position, the surgeon may: drill the tibia to receive a fourth set of pins according to the second set of tibial pin guides 172 defined by the conforming bearing 170; remove the conforming bearing 170 from the tibia; locate the longitudinal tibial cut guide 180 on the tibia via the fourth set of pins; and drill or ream a longitudinal bore—along the longitudinal tibial cut axis 182 defined by the longitudinal tibial cut guide 180—through the tibia; and finally install the artificial tibial component 190 in the knee with the stem 193 of the artificial tibial component 190 inserted into the bore and the inner proximal tibial face 191 of the artificial tibial component 190 in contact with the resected proximal tibial face of the tibia.

The surgeon may then verify tension on the medial and lateral ligaments, locate the patella, and close the knee to complete the surgery.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:
1. A system for total knee replacement comprising:
   a proximal tibial alignment guide:
      configured to locate on a tibia of a leg in extension;
      defining a first set of tibial pin guides configured to guide location of a first set of pins on the tibia; and
      defining a tibial reference surface relative to the first set of tibial pin guides;
   a distal femoral alignment guide:
      configured to locate on a femur of the leg in extension;
      constrained relative to the proximal tibial alignment guide by the tibial reference surface; and
      defining a first set of femoral pin guides, relative to the first set of tibial pin guides, configured to guide location of a second set of pins on the femur;
   a proximal tibial cut guide:
      configured to locate on the tibia via the first set of pins; and
      defining a proximal tibial cut plane for resecting a proximal structure of the tibia to form a resected proximal tibial face;
   a distal femoral cut guide:
      configured to locate on the femur via the second set of pins; and
      defining a distal femoral cut plane, linearly offset from the proximal tibial cut plane, for resecting a distal structure of the femur to form a resected distal femoral face;
   an intermediate femoral alignment guide:
      configured to insert between the tibia and the femur in partial flexion;
      comprising a tibial side configured to mate with the resected proximal tibial face;
      comprising a femoral side angularly offset from the tibial side by an intermediate angle and configured to mate with the resected distal femoral face; and
      defining a second set of femoral pin guides, relative to the tibial side and the femoral side, configured to guide location of a third set of pins on the femur; and
   a posterior femoral cut guide:
      configured to locate on the third set of pins; and
      defining a posterior femoral cut plane, angularly offset from the resected distal femoral face, for resecting a posterior structure of the tibia to form a resected distal femoral face.

2. The system for total knee replacement of claim 1, further comprising:
   an artificial tibial component:
      defining an inner proximal tibial face:
         configured to mate with the resected proximal tibia face; and
         constrained by the resected proximal tibia face in translation along a tibial longitudinal axis, in rotation about a tibial medial-lateral axis, and in rotation about a tibial anteroposterior axis; and
      defining a tibial mating surface; and
   an artificial femoral component:
      defining an inner distal femoral face:
         configured to mate with the resected distal femoral face; and
         constrained by the resected distal femoral face in translation along a femoral longitudinal axis, in rotation about a femoral medial-lateral axis, and in rotation about a femoral anteroposterior axis;

defining an inner posterior femoral face:
  configured to mate with the resected posterior femoral face; and
  constrained by the resected posterior femoral face in translation along the femoral anteroposterior axis and in rotation about the femoral longitudinal axis; and
defining a femoral mating surface configured to mate with and slide along the tibial mating surface.

3. The system for total knee replacement of claim 2:
  wherein the intermediate femoral alignment guide defines a nominal geometry between the tibial side and the femoral side that approximates a first target geometry between the inner proximal tibial face of the artificial tibial component and the inner distal femoral face of the artificial femoral component when the artificial tibial component and the artificial femoral component are assembled and form the intermediate angle; and
  wherein the posterior femoral cut guide defines the posterior femoral cut plane relative to the distal femoral face, when located on the femur via the third set of pins, according to a position of the inner posterior femoral face of the artificial femoral component relative to the inner distal femoral face of the artificial femoral component.

4. The system for total knee replacement of claim 1, wherein the intermediate femoral alignment guide forms a wedge geometry that forms the intermediate angle between 55° and 65° between the tibial side and the femoral side to mate with the resected proximal tibial face and the resected distal femoral face in partial flexion between 55° and 65° from extension.

5. The system for total knee replacement of claim 1, wherein the proximal tibial alignment guide:
  defines a medial window configured to pass a medial tensioner that contacts a medial side of the proximal structure of the tibia and a medial side of the distal structure of the femur to tension a medial ligament of a knee in the leg prior to location of the distal femoral alignment guide on the femur; and
  defines a lateral window configured to pass a lateral tensioner that contacts a lateral side of the proximal structure of the tibia and a lateral side of the distal structure of the femur to tension a lateral ligament of the knee prior to location of the distal femoral alignment guide on the femur.

6. The system for total knee replacement of claim 5:
  wherein the proximal tibial alignment guide is configured to locate on the tibia and the distal femoral alignment guide is configured to locate on the femur with the knee located in extension, the medial ligament tensioned to a target extension tension, and the lateral ligament tensioned to the target extension tension;
  wherein the tibial reference surface locates the distal femoral alignment guide with the first set of pin guides distally offset from the second set of pin guides by a first distance;
  wherein the proximal tibial cut guide:
    locates on the tibia via the first set of pins; and
    defines the proximal tibial cut plane offset from the first set of pins by a second distance;
  wherein the distal femoral tibial cut guide:
    locates on the femur via the second set of pins; and
    defines the distal femoral cut plane parallel to the proximal tibial cut plane and offset from the first set of pins by a third distance; and
  wherein a sum of the second distance, the third distance, and a target combined height of an artificial tibial component and an artificial femoral component in extension approximates the first distance to produce the target extension tension on the medial ligament and the lateral ligament with the artificial tibial component and the artificial femoral component installed in the knee and with the knee in extension.

7. The system for total knee replacement of claim 5, wherein the intermediate femoral alignment guide:
  defines a second medial window configured to pass a second medial tensioner that contacts a medial side of the resected proximal tibial face and a medial side of the resected distal femoral face to tension the medial ligament prior to the tibial side of the intermediate femoral alignment guide seating on the resected proximal tibial face and the femoral side of the intermediate femoral alignment guide seating on the resected distal femoral face; and
  defines a second lateral window configured to pass a second lateral tensioner that contacts a lateral side of the resected proximal tibial face and a lateral side of the resected distal femoral face to tension the lateral ligament prior to the tibial side of the intermediate femoral alignment guide seating on the resected proximal tibial face and the femoral side of the intermediate femoral alignment guide seating on the resected distal femoral face.

8. The system for total knee replacement of claim 7:
  wherein the proximal tibial alignment guide is configured to locate on the tibia and the distal femoral alignment guide is configured to locate on the femur with the knee located in extension, the medial ligament tensioned to a target extension tension, and the lateral ligament tensioned to the target extension tension; and
  wherein the intermediate femoral alignment guide is configured to seat against the resected proximal tibial face and the resected distal femoral face with the knee located in partial flexion, the medial ligament tensioned to a target partial-flexion tension, and the lateral ligament tensioned to the target partial-flexion tension.

9. The system for total knee replacement of claim 8:
  wherein the intermediate femoral alignment guide defines a nominal geometry between the tibial side and the femoral side that approximates a first target geometry between an inner proximal tibial face of an artificial tibial component and an inner distal femoral face of an artificial femoral component when the artificial tibial component and the artificial femoral component are assembled and form the intermediate angle;
  wherein the intermediate femoral alignment guide defines the second set of femoral pin guides at a first offset from the tibial side and the femoral side;
  wherein the posterior femoral cut guide defines the posterior femoral cut plane at a second offset from the third set of pins when located on the femur; and
  wherein a sum of the first offset and the second offset approximates relative positions of the inner proximal tibial face of the artificial tibial component, the inner distal femoral face of the artificial femoral component, and an inner posterior femoral face of the artificial femoral component when the artificial tibial component and the artificial femoral component form the intermediate angle to produce the target partial-flexion tension on the medial ligament and the lateral ligament with the artificial tibial component and the artificial femoral component installed in the knee and with the knee forming the intermediate angle.

10. The system for total knee replacement of claim 1:
wherein the proximal tibial alignment guide is configured to locate on the tibia and the distal femoral alignment guide is configured to locate on the femur with the knee located in extension, a medial ligament of a knee in the leg tensioned to a target extension tension, and a lateral ligament of the knee tensioned to a target extension tension;
wherein the tibial reference surface locates the distal femoral alignment guide with the first set of pin guides distally offset from the second set of pin guides by a first distance;
wherein the proximal tibial cut guide:
locates on the tibia via the first set of pins; and
defines the proximal tibial cut plane offset from the first set of pins by a second distance;
wherein the distal femoral tibial cut guide:
locates on the femur via the second set of pins; and
defines the distal femoral cut plane parallel to the proximal tibial cut plane and offset from the first set of pins by a third distance;
wherein a first sum of the second distance, the third distance, and a target combined distance between an inner proximal tibial face of an artificial tibial component and an inner distal femoral face of an artificial femoral component approximates the first distance to produce the target extension tension on the medial ligament and the lateral ligament with the artificial tibial component and the artificial femoral component installed in the knee and with the knee in extension;
wherein the intermediate femoral alignment guide defines a nominal geometry between the tibial side and the femoral side that approximates a first target geometry between the inner proximal tibial face of the artificial tibial component and the inner distal femoral face of the artificial femoral component when the artificial tibial component and the artificial femoral component are assembled and form the intermediate angle;
wherein the intermediate femoral alignment guide defines the second set of femoral pin guides at a first offset from the tibial side and the femoral side;
wherein the posterior femoral cut guide defines the posterior femoral cut plane at a second offset from the third set of pins when located on the femur; and
wherein a second sum of the first offset and the second offset approximates relative positions of the inner proximal tibial face of the artificial tibial component, the inner distal femoral face of the artificial femoral component, and the inner posterior femoral face of the artificial femoral component when the artificial tibial component and the artificial femoral component are assembled and form the intermediate angle to produce the target partial-flexion tension on the medial ligament and the lateral ligament with the artificial tibial component and the artificial femoral component installed in the knee and with the knee forming the intermediate angle.

11. The system for total knee replacement of claim 1, further comprising an ankle alignment indicator:
extending distally from the proximal tibial alignment guide;
configured to indicate an angular offset about a tibial anteroposterior axis and a tibial medial-lateral axis between a mechanical axis of the tibia and the proximal tibial cut plane, defined by the proximal tibial cut guide located on the tibia via the first set of pins, prior to placement of the proximal tibial cut guide on the tibia and prior to resection of the proximal structure of the tibial; and
configured to indicate an angular offset about a femoral anteroposterior axis and a femoral medial-lateral axis between the mechanical axis of the tibia and the distal femoral cut plane, defined by the distal femoral cut guide located on the femur via the second set of pins, prior to placement of the distal femoral cut guide on the femur and prior to resection of the distal structure of the femur, the distal femoral cut plane parallel to and linearly offset from the proximal tibial cut plane.

12. The system for total knee replacement of claim 1:
wherein the proximal tibial alignment guide defines the first set of tibial pin guides for drilling a first set of bores into the tibia to receive the first set of pins; and
wherein the distal femoral alignment guide:
mates with and is constrained by the tibial reference surface:
in rotation about a medial-lateral axis of the proximal tibial alignment guide; and
in rotation about an anteroposterior axis of the proximal tibial alignment guide; and
defines the second set of tibial pin guides for drilling a second set of bores into the femur, relative to the first set of bores, to receive the second set of pins.

13. The system for total knee replacement of claim 12, wherein the proximal tibial alignment guide defines the tibial reference surface configured to constrain the distal femoral alignment guide in translation along a longitudinal axis of the proximal tibial alignment guide over a range of linear distances selectable according to a target combined height of an artificial tibial component and an artificial femoral component in extension.

14. The system for total knee replacement of claim 12:
wherein the proximal tibial alignment guide defines the tibial reference surface configured to constrain the distal femoral alignment guide in translation along a longitudinal axis of the proximal tibial alignment guide;
wherein the proximal tibial cut guide is constrained on the tibia by the first set of pins:
in rotation about a medial-lateral axis of the tibia;
in rotation about an anteroposterior axis of the tibia; and
in translation over a first range of linear distances along a longitudinal axis of the tibia according to a height of an artificial tibial component; and
wherein the proximal tibial cut guide is constrained on the femur by the second set of pins:
in rotation about a medial-lateral axis of the femur;
in rotation about an anteroposterior axis of the femur; and
in translation over a second range of linear distances along a longitudinal axis of the femur according to a height of an artificial femoral component.

15. The system for total knee replacement of claim 1, wherein the proximal tibial alignment guide comprises:
a medial indicator configured for alignment with a medial interstice between a medial tibial plateau and a medial femoral condyle during location of the proximal tibial alignment guide on the tibia; and
a lateral indicator configured for alignment with a lateral interstice between a lateral tibial plateau and a lateral femoral condyle during location of the proximal tibial alignment guide on the tibia.

16. The system for total knee replacement of claim 15:
wherein the proximal tibial alignment guide defines the first set of tibial pin guides longitudinally offset from the medial indicator and the lateral indicator by a first distance;
wherein the proximal tibial cut guide:
   locates on the tibia via the first set of pins; and
   defines the proximal tibial cut plane longitudinally offset from the first set of pins by a second distance;
wherein a first sum of the second distal distance and an effective height of an artificial tibial component in extension approximates the first distance;
wherein the distal femoral alignment guide:
   locates on the proximal tibial alignment guide by the tibial reference surface; and
   defines the second set of femoral pin guides longitudinally offset from the medial indicator and the lateral indicator by a third distance when located by the tibial reference surface;
wherein the distal femoral cut guide:
   locates on the femur via the second set of pins; and
   defines the distal femoral cut plane longitudinally offset from the second set of pins by a fourth distance; and
wherein a second sum of the fourth distal distance and an effective height of an artificial femoral component in extension approximates the third distance.

17. The system for total knee replacement of claim 1, further comprising:
a conforming bearing:
   defining a proximal concave face configured to mesh with a distal convex face of an artificial femoral component installed over the resected distal femoral face;
   defining a distal face configured to slide on the resected proximal tibial face to seat in a ligament-balancing position on the resected proximal tibial face as the tibia is moved over a range of motion relative to the femur, a medial ligament and a lateral ligament in the leg approaching minimum peak tensions over the range of motion with the conforming bearing occupying the ligament-balancing position on the resected proximal tibial face; and
   defining a second set of tibial pin guides configured to guide location of a fourth set of pins on the tibia; and
a longitudinal tibial cut guide:
   configured to locate on the tibia via the fourth set of pins; and
   defining a longitudinal tibial cut axis for boring the tibia to receive a stem of an artificial tibia component.

18. The system for total knee replacement of claim 17:
wherein the conforming bearing defines:
   a nominal geometry that approximates a target geometry of a proximal section of an artificial tibial component configured to seat over the resected proximal tibial face; and
   the second set of tibial pin guides at a first offset from the proximal concave face;
wherein the longitudinal tibial cut guide defines the longitudinal tibial cut axis at a second offset from the fourth set of pins; and
wherein a sum of the first offset and the second offset approximates a position of a stem of the artificial tibial component relative to the proximal section of the artificial tibial component to locate the artificial tibial component in the ligament-balancing position on the tibia over the range of motion of a knee.

19. A system for total knee replacement comprising:
a first alignment guide:
   configured to locate on a first bone of a joint in extension;
   defining a first set of pin guides configured to guide location of a first set of pins on the first bone; and
   defining a first reference surface relative to the first set pin guides;
a second alignment guide:
   configured to locate on a second bone of the joint in extension;
   constrained relative to the first alignment guide by the first reference surface; and
   defining a second set of pin guides, relative to the first set pin guides, configured to guide location of a second set of pins on the second bone; and
a first cut guide:
   configured to locate on the first bone via the first set of pins; and
   defining a first cut plane for resecting the first bone to form a first resected face on the first bone;
a second cut guide:
   configured to locate on the second bone via the second set of pins; and
   defining a second cut plane, linearly offset from the first cut plane, for resecting the second bone to form a second resected face on the second bone;
a third alignment guide:
   configured to insert between the first bone and the second bone in partial flexion;
   comprising a first side configured to mate with the first resected face;
   comprising a second side angularly offset from the first side by an intermediate angle and configured to mate with the second resected face; and
   defining a third set of pin guides, relative to the first side and the second side, configured to guide location of a third set of pins on the second bone;
a third cut guide:
   configured to locate on the third set of pins; and
   defining a posterior cut plane, angularly offset from the second resected face, for resecting a posterior structure of the first bone to form a third resected face on the second bone;
a conforming bearing:
   defining a concave face configured to mesh with a convex face of a first artificial joint component installed over the first resected face of the first bone;
   defining a second face, opposite the convex face, configured to slide on the first resected face to seat in a ligament-balancing position on the first resected face as the first bone is moved over a range of motion relative to the second mode; and
   defining a fourth set of pin guides configured to guide location of a fourth set of pins on the first bone; and
a fourth cut guide:
   configured to locate on the first bone via the fourth set of pins; and
   defining a longitudinal cut axis for boring the first bone to receive a stem of the first artificial joint component.

20. A system for total knee replacement comprising:
an artificial tibial component defining an inner proximal tibial face;

an artificial femoral component defining an inner distal femoral face, an inner posterior femoral face, and an inner anterior face and configured to mate with the artificial tibial component;

a first guide unit configured for temporary installation on a tibia and defining a proximal tibial cut guide that locates a blade during resection of the tibia to form a proximal tibial face;

a second guide unit:
- configured to reference against the first guide unit;
- configured for temporary installation on a femur; and
- defining a distal femoral cut guide offset from the proximal tibial cut guide by a distance between the inner proximal tibial face of the artificial tibial component and the inner distal femoral face of the artificial femoral component in an extension position and that locates a blade during resection of the femur to form a distal femoral face; and a third guide unit:
- defining a tibial-side face configured to mate against the proximal tibial face;
- defining a femoral-side face configured to mate against the distal femoral face and angularly offset from the tibial-side face by an intermediate angle between flexion and extension;
- defining a wedge-geometry between the tibial-side face and the femoral-side face corresponding to a geometry between the inner proximal tibial face of the artificial tibial component and the inner distal femoral face of the artificial femoral component in the intermediate position; and
- defining a posterior femoral cut guide positioned relative to the femoral-side face according to a position of the posterior inner face relative to the distal inner face of the artificial femoral component and that locates a blade during resection of the femur to form a posterior femoral face.

* * * * *